US007402726B2

(12) United States Patent
Pallanck et al.

(10) Patent No.: US 7,402,726 B2
(45) Date of Patent: Jul. 22, 2008

(54) METHODS AND COMPOSITIONS FOR SCREENING FOR MODULATORS OF PARKINSON'S DISEASE

(75) Inventors: Leo J. Pallanck, Seattle, WA (US); Jessica G. Zuniga, Redmond, WA (US); Alexander J. Whitworth, Seattle, WA (US)

(73) Assignee: The University of Washington, Seattle, WA (US)

( * ) Notice: Subject to any disclaimer, the term of this patent is extended or adjusted under 35 U.S.C. 154(b) by 256 days.

(21) Appl. No.: 11/054,358

(22) Filed: Feb. 8, 2005

(65) Prior Publication Data
US 2006/0101527 A1 May 11, 2006

Related U.S. Application Data

(60) Provisional application No. 60/626,810, filed on Nov. 9, 2004.

(51) Int. Cl.
*A01K 67/00* (2006.01)
*A01K 67/033* (2006.01)
(52) U.S. Cl. .......................................... 800/8; 800/13
(58) Field of Classification Search .................. 800/8, 800/13
See application file for complete search history.

(56) References Cited

U.S. PATENT DOCUMENTS

| 6,812,248 | B2 | 11/2004 | Zhang et al. | |
| 6,943,278 | B2 * | 9/2005 | Chung | 800/13 |
| 2004/0073955 | A1 * | 4/2004 | Chung | 800/13 |
| 2004/0205833 | A1 | 10/2004 | Klein et al. | |
| 2006/0174356 | A1 | 8/2006 | Pallanck et al. | |

OTHER PUBLICATIONS

Cordato (J. Clinical Nuerosci., Feb. 2004, vol. 11, No. 2, p. 119-123).*
Lockhart (Movement disorders, Jan. 2004, vol. 19, No. 1, p. 101-104).*
Whitworth (PNAS, May 31, 2005, vol. 102, No. 22, p. 8024-8029).*
Stroombergen et al. Determination of glutathione S-transferease μ and O polymorphisms in neurological disease. Human & Experimental Toxicology (1999) vol. 18, pp. 141-145.
Auluck et al., Pharmacological prevention of Parkinson disease in Drosophila, Nat. Med. 8(11):1185-1186 (2002).
Feany et al., "A drosophila model of parkinson' s disease", Nature, 404(6776):394-398 (2000).
Giasson et al., "Are ubiquitination pathways central to parkinson's disease", Cell, 114(1):1-8 (2003).
Giasson et al., "Parkin and the molecular pathways of parkinson's disease", Neuron, 31(6):885-888 (2001).
Goldberg et al., "Is there a cause-and-effect relationship between α-synuclein fibrillization and parkinson'disease", Nat. Cell Biol., 2(7):E115-119 (2000).
Greene et al., "Mitochondrial pathology and apoptotic muscle degeneration in drosophila parkin mutants", PNAS, 100(7):4078-4083 (2003).
Haywood et al., "Parkin counteracts symptoms in a drosophila model of parkinson's disease", BMC Neuroscience, 5:14 (2004).
Link, "Transgenic invertebrate models of age-associated neurodegenerative diseases", Mech. Ageing Dev., 122(14):1639-1649 (2001).
Muqit et al., "Modeling neurodegenerative diseases in drosophila: a fruitful approach", Nat. Rev. Neurosci., 3(3):237-243 (2002).
Pendleton et al., "Effects of pharmacological agents upon a transgenic model of parkinson's disease in drosophila melanogaster", J. Pharm. Exper. Ther., 300(1): 91-96 (2002).
Pesah et al., "Drosophila parkin mutants have decreased mass and cell size and increased sensitivity to oxygen radical stress", Development and Disease 131(9):2183-2194 (2004).
Scherzer et al., "Gene expression changes presage neurodegeneration in a drosophila model of parkinson's disease", Hum. Mol. Genetics, 12(19):2457-2466 (2003).
Wanker, "Protein aggregation in huntington's and parkinson's disease: implications for therapy", Mol. Med. Today, 6(10):387-391 (2000).
West et al., "Genetics of parkin-linked disease", Hum. Genet., 114(4):327-336 (2004).
Deng Y. et al. Case-only study of interactions between genetic polymorphisms of GSTM1, P1, T1 and Z1 and smoking in Parkinson's disease. Neurosci Lett. Aug. 19, 2004;366(3):326-31.
Haass and Kahle. Parkinson's pathology in a fly.Nature, Mar. 23, 2000;404(6776):341, 343.
Hattori et al. Pathogenetic mechanisms of parkin in Parkinson's disease. Lancet. Aug. 21-27, 2004;364(9435):722-4.
Kelada et al. Glutathione S-transferase M1, T1, and P1 polymorphisms and Parkinson's disease. Neurosci Lett. Jan. 30, 2003;337(1):5-8.
Li et al. Glutathione S-transferase omega-1 modifies age-at-onset of Alzheimer disease and Parkinson disease. Hum Mol Genet. Dec. 15, 2003;12(24):3259-67. Epub Oct. 21, 2003.
Menegon et al. Parkinson's disease, pesticides, and glutathione transferase polymorphisms. Lancet. Oct. 24, 1998;352(9137):1344-6.
von Bohlen Und Halbach O. Prog Neurobiol. Genes, proteins, and neurotoxins involved in Parkinson's disease. Jun. 2004;73(3):151-77.
Vila A. and S. Przedborski. Genetic clues to the pathogenesis of Parkinson's disease. Nat Med. Jul. 2004;10 Suppl:S58-62.

* cited by examiner

*Primary Examiner*—Michael C. Wilson
(74) *Attorney, Agent, or Firm*—Carol L. Francis; Bozicevic, Field & Francis LLP

(57) ABSTRACT

Methods and compositions for identifying an agent (e.g., a gene product or small molecule compound) that modulates a Parkinson's disease phenotype are provided. In practicing the subject methods, a non-mammalian animal model, such as *Drosophila melanogaster*, that includes a mutant parkin gene and at least one other mutant gene are evaluated for a Parkinson's disease phenotype. Also provided are kits, and systems for practicing the subject methods, as well as methods of use of agents identified in the screening method of the invention.

5 Claims, 8 Drawing Sheets

A.

B.

C.

A.

B.

Interactions between *parkin* and array-identified genes

METHODS AND COMPOSITIONS FOR SCREENING FOR MODULATORS OF PARKINSON'S DISEASE

CROSS-REFERENCE

This application claims the benefit of U.S. Provisional Application Ser. No. 60/626,810, filed Nov. 9, 2004, which application is incorporated herein by reference in its entirety.

GOVERNMENT RIGHTS

This invention was made with government support under federal grant Nos. 1RO1NS41780-01 awarded by National Institutes of Health. The United States Government may have certain rights in this invention.

BACKGROUND OF THE INVENTION

Parkinson's disease (PD) is a common neurodegenerative disorder characterized by the loss of dopaminergic (DA) neurons in the substantia nigra pars compacta. There is evidence for oxidative stress, mitochondrial dysfunction, aberrant proteolytic processes and dysfunctional immune surveillance playing roles in the pathogenesis of PD, however the molecular mechanisms of the involvement of these processes are currently unclear. Although most PD is sporadic, recent work has led to the identification of heritable forms of this disorder. The identification of genes associated with these heritable forms of PD has shed light on processes thought to be important for degeneration in sporadic PD, and analysis of genes that are mutated in heritable forms of PD has begun to further define molecular mechanisms of pathogenesis.

Loss-of-function mutations in the parkin gene have been shown to be a major cause for early onset PD, and there is increasing evidence for the role of Parkin in late-onset and sporadic PD as well. Parkin has been shown to be an E3 ligase in the ubiquitin protein degradation pathway, which suggests that accumulation of Parkin substrates leads to the death of dopaminergic neurons.

It has been demonstrated that *Drosophila* parkin null mutants exhibit flight muscle degeneration with accompanying mitochondrial pathology (Greene et al., PNAS, 100(7): 4078-4083 (2003)). The most striking phenotype resulting from loss of *Drosophila* parkin function is apoptotic muscle degeneration. Ultrastructural analysis of *Drosophila* parkin mutants demonstrated profound mitochondrial pathology in flight muscle and the male germline. Parkin mutants also show partial pupal lethality and locomotor phenotypes which are rescued by expression of a parkin cDNA in muscle tissue.

To date, nine substrates of Parkin have been identified, pointing to a variety of hypotheses about the role that Parkin plays in the cell. Some of the identified substrates implicate specific cellular pathways in parkin etiology. For example, the putative G-protein coupled receptor Pael-R was identified as a substrate of Parkin. As accumulation of Pael-R induces the unfolded-protein response/endoplasmic reticulum (ER) stress, this suggests that ER stress plays a role in Parkin pathology. Cyclin E has also been identified as a Parkin substrate, and a buildup of Cyclin E could lead to inappropriate activation of the cell cycle and subsequent apoptosis of DA neurons. Metabolism of Lewy body components has also been suggested as a role for Parkin by the demonstration that an o-glycosylated form of α-synuclein and the α-synuclein-interacting protein Synphilin can be Parkin substrates as well. Though the identification of Parkin substrates suggests pathways which may be important in pathology, the roles of these factors in Parkin pathogenesis is not well defined. The number of substrates identified and the lack of correspondence in studies investigating some of these factors further confounds any conclusions to be drawn about their role in Parkin pathogenesis.

Accordingly, there remains a need in this art for developing non-human animal models and methods for identifying agents that affect the PD phenotype, including methods for screening agents for use in treating Parkinson's disease, and the like. The present invention addresses this need.

Relevant Literature

U.S. patents of interest include: U.S. Pat. No. 6,812,248. Published U.S. Applications of interest include: 20040205833. Additional references of interest include: Greene et al., PNAS, 100(7):4078-4083 (2003); Haywood et al., BMC Neuroscience, 5:14 (2004); Pendleton et al., J. Pharm. Exper. Ther., 300(1):91-96 (2002); Pesah et al., Development 131(9):2183-2194 (2004); West et al., Hum. Genet., 114(4):327-336 (2004); Scherzer et al., Hum. Mol. Genetics, 12(19):2457-2466 (2003); Giasson et al., Cell, 114 (1):1-8 (2003); Auluck et al., Nat. Med. 8(11):1185-1186 (2002); Muqit et al., Nat. Rev. Neurosci., 3(3):237-243 (2002); Giasson et al., Neuron, 31(6):885-888 (2001); Link, Mech. Ageing Dev., 122(14):1639-1649 (2001); Wanker, Mol. Med. Today, 6(10):387-391 (2000); Goldberg et al., Nat. Cell Biol., 2(7):E115-119 (2000); and Feany et al., Nature, 404(6776):394-398 (2000).

SUMMARY OF THE INVENTION

Methods and compositions for identifying an agent (e.g., a gene product or small molecule compound) that modulates a Parkinson's disease phenotype are provided. In practicing the subject methods, a non-mammalian animal model, such as *Drosophila melanogaster*, that includes a mutant parkin gene and at least one other mutant gene are evaluated for a Parkinson's disease phenotype. Also provided are kits, and systems for practicing the subject methods, as well as methods of use of agents identified in the screening method of the invention.

In one aspect, the invention features a method for identifying a gene that modulates a Parkinson's disease phenotype, including evaluating a Parkinson's disease phenotype in a non-mammalian animal model having a non-functional mutant parkin gene and a defect in at least one other gene. A change in the Parkinson's disease phenotype in the non-mammalian animal model as compared to an appropriate control (e.g., without a mutation in a non-parkin gene or in a gene known not to affect a PD phenotype) indicates that the defective non-parkin gene modulates the Parkinson's disease phenotype. In certain embodiments, the animal model is an invertebrate animal. In further embodiments, the invertebrate animal is a member of the family Drosophilidae. In further embodiments the invertebrate animal is a *Drosophila melanogaster*.

In some embodiments, the defect in at least one other gene is generated by P element transposon insertion. In other embodiments, the Parkinson's disease phenotype includes viability of progeny, the climbing capability of the non-mammalian animal model, the flight capability of the non-mammalian animal model, and the like. In further embodiments, the modulating results in enhancing the Parkinson's disease phenotype. In still other embodiments, the modulating results in suppressing the Parkinson's disease phenotype.

In another feature the invention provides a non-mammalian animal model for Parkinson's disease having a nonfunctional mutant parkin gene and a non-functional mutation in at least one other gene. In some embodiments the non-parkin gene is a glutathione S-transferase S1 gene. In certain embodiments, the animal model is an invertebrate animal. In further embodiments, the invertebrate animal is a member of the family Drosophilidae. In further embodiments the invertebrate animal is a *Drosophila melanogaster*.

In yet another feature the invention provides a method for screening for an agent that modulates a Parkinson's disease phenotype, including administering an agent to a non-mammalian animal model having a non-functional mutant parkin gene and a defect in at least one other gene, and evaluating the non-mammalian animal model for a Parkinson's disease phenotype, wherein a change in the Parkinson's disease phenotype in the non-mammalian animal model in the presence of the agent as compared to a non-mammalian in the absence of the agent indicates that the agent modulates the Parkinson's disease phenotype. In some embodiments the defective non-parkin gene is a glutathione S-transferase S1 gene. In certain embodiments, the animal model is an invertebrate animal. In further embodiments, the invertebrate animal is a member of the family Drosophilidae. In further embodiments the invertebrate animal is a *Drosophila melanogaster*.

In some embodiments, the Parkinson's disease phenotype includes viability of progeny, the climbing capability of the non-mammalian animal model, the flight capability of the non-mammalian animal model, and the like. In some embodiments, the modulating results in enhancing the Parkinson's disease phenotype. In other embodiments, the modulating results in suppressing the Parkinson's disease phenotype.

Yet another feature of the invention provides a method for screening for an agent that increases the level of glutathione S-transferase (GST) or otherwise enhances GST activity, including administering an agent to a non-mammalian animal model having a non-functional mutant parkin gene and a mutant (e.g., defective or non-functional) glutathione S-transferase gene, and evaluating the non-mammalian animal model for a Parkinson's disease phenotype, wherein a change in the Parkinson's disease phenotype in the non-mammalian animal model in the presence of the agent as compared to the absence of the agent indicates that the agent increases the level of glutathione S-transferase or enhances GST activity. Agents that improve GSTS1 bioavailability and/or activity are of particular interest. In certain embodiments, the animal model is an invertebrate animal. In further embodiments, the invertebrate animal is a member of the family Drosophilidae. In further embodiments the invertebrate animal is a *Drosophila melanogaster*.

In some embodiments, the Parkinson's disease phenotype includes viability of progeny, the climbing capability of the non-mammalian animal model, the flight capability of the non-mammalian animal model, and the like. In some embodiments, the modulating results in enhancing the Parkinson's disease phenotype. In other embodiments, the modulating results in suppressing the Parkinson's disease phenotype.

These and other features and advantages of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
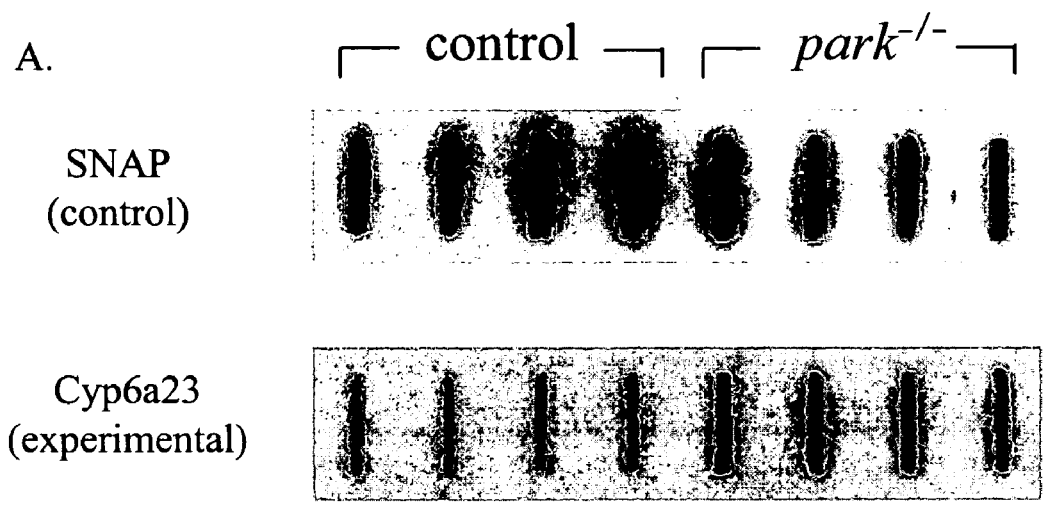
FIG. 1 shows slot blot analysis of transcripts in parkin mutants and controls. Panel A shows representative images from slot blot analysis showing control (SNAP) and experimental (Cyp6a23) probe signal intensities from parkin wild-type and parkin mutant RNA samples. SNAP expression is unaltered in parkin mutant pupae and serves as a loading control for these analyses. Panel B shows a quantification of slot blot data, which shows altered levels of experimental RNA in parkin mutants compared to control. Dark bars represent controls (park$^{rvA}$/park$^{rvA}$) and white bars represent parkin mutants (park$^{25}$/park$^{25}$). Asterisk indicates that the right-hand Y axes should be used for the data for CG12505.
Figure 1:
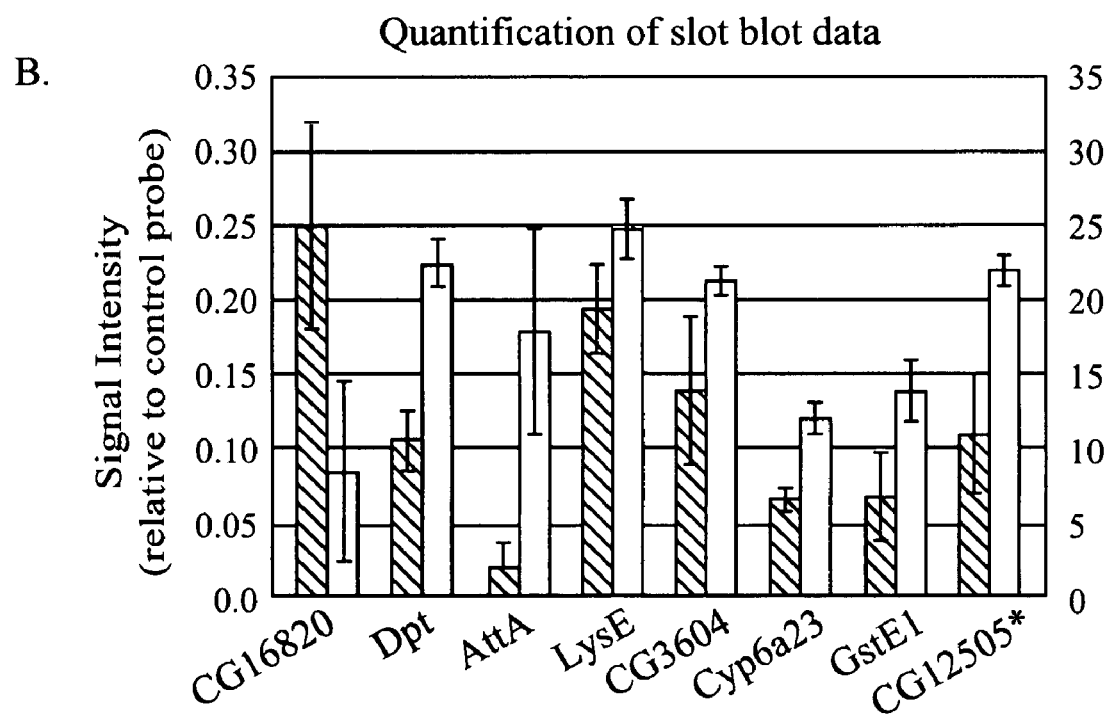

Methods and compositions for identifying an agent (e.g., a gene product or small molecule compound) that modulates a Parkinson's disease phenotype are provided. In practicing the subject methods, a non-mammalian animal model, such as

*Drosophila melanogaster*, that includes a mutant parkin gene and at least one other mutant gene are evaluated for a Parkinson's disease phenotype. Also provided are kits and systems for practicing the subject methods, as well as methods of use of agents identified in the screening method of the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an individual" includes one or more individuals and reference to "the method" includes reference to equivalent steps and methods known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The phrase "degenerative disease," as used in the current context, is readily understood by one of ordinary skill in the art, and is used to mean any physiological condition that may be characterized by the death or dysfunction of normal cells in the affected tissue. Unless specifically indicated otherwise, a degenerative disease is not used to mean a disease where the death of the normal cells is caused by tumor growth or acute toxic insult. Examples of degenerative disorders include, but are not limited to, diabetes, chronic liver failure, chronic kidney failure, Wilson's disease, congestive heart failure and atherosclerosis and any neurodegenerative disease.

A neurodegenerative disease, as used in the current context, is readily understood by one of ordinary skill in the art to include any abnormal physical or mental behavior or experience where the death or dysfunction of neuronal cells is involved in the etiology of the disorder, or is affected by the disorder. As used herein, neurodegenerative diseases encompass disorders affecting the central and peripheral nervous systems, and include such afflictions as memory loss, stroke, dementia, personality disorders, gradual, permanent or episodic loss of muscle control. Examples of neurodegenerative diseases for which the current invention can be used preferably include, but are not limited to, Alzheimer's Disease, Parkinson's Disease, Huntington's Disease, amyotrophic lateral sclerosis, epilepsy, myasthenia gravis, neuropathy, ataxia, dementia, chronic axonal neuropathy and stroke.

As used herein "Parkinson's disease" refers to condition of disturbance of voluntary movement in which muscles become stiff and sluggish, movement becomes clumsy and difficult and uncontrollable rhythmic twitching of groups of muscles produces characteristic shaking or tremor. The condition is believed to be caused by a degeneration of pre-synaptic dopaminergic neurons in the brain. The absence of adequate release of the chemical transmitter dopamine during neuronal activity thereby leads to the Parkinsonian symptomatology.

The term "cell death" as used herein means a process or event that causes the cell to cease or diminish normal metabolism in vivo or in vitro. The various forms and signs of cell death are obvious to those skilled in the art, but examples of cell death include, but are not limited to, programmed cell death (i.e., apoptosis), gradual death of the cells as occurs in diseased states (i.e., necrosis), and more immediate cell death such as acute toxicity. The inhibition of cell death for which the current invention provides can be a complete or partial inhibition of cell death. Likewise, the inhibition of cell death for which the current invention provides can be a complete or partial reversal of the process of cell death.

The term "cell dysfunction" or "cellular dysfunction" means a cellular process or event that is less profound than cell death. This includes but is not limited to synaptic or dendritic degeneration, reduced cell function such as synaptic, metabolic or bioenergetic reduction, and/or organelle degeneration or dysfunction.

As used herein, neuronal cells include cells of the central and peripheral nervous systems, including the two classes of neurons and glial cells. Within each class of cells, there are unique types of cells that one of ordinary skill in the art would recognize such as oligodendrocytes, astrocytes, Schwann cells, and dopaminergic neurons.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The terms "reference" and "control" are used interchangeably to refer to a known value or set of known values against which an observed value may be compared. As used herein, known means that the value represents an understood parameter, e.g., a level of expression of a cytotoxic marker gene in the absence of contact with a transfection agent.

As used herein, "treatment" or "treating" refers to inhibiting the progression of a disease or disorder, e.g., Parkinson's disease, or delaying the onset of a disease or disorder, e.g., Parkinson's disease, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated with Parkinson's disease.

As used herein, the phrase "increased or decreased expression" is used to mean an increase or decrease in the transcription of one or more genes of interest, resulting in an increase or decrease in the levels of mRNA for each gene, respectively. The phrase is also used to mean an increase or decrease in the levels of the corresponding gene product (e.g., protein) in the cell, independent of transcription levels or rates. For example, an increase in degradation rate of an mRNA encoding the protein in question, without a change in the transcription rate, may result in a decrease in the levels of protein in the cell.

The term "isolated compound" means a compound which has been substantially separated from, or enriched relative to, other compounds with which it occurs in nature. Isolated compounds are usually at least about 80%, more usually at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof.

By "parkin" gene is meant the gene that encodes the ubiquitin-protein ligase, which when is non-function is the common cause of Autosomal Recessive Juvenile Parkinsonism (AR-JP). Further information on the parkin gene can be found in Greeene et al., 2003, and Fishman et al., Curr. Neurol. Neurosci. Rep. 2(4):296-302 (2002), the disclosures of which are incorporated herein in their entirety by reference. The nucleotide sequence for the human park gene is available at GenBank Accession No. NM_013987, and the nucleotide sequence for the Drosophila park gene is available at GenBank Accession No. NM_168885.

By "parkin defect", or a "defective" or "mutant" parkin gene, is meant a parkin gene that does not provide for production of a functional Parkin gene product, e.g., due to naturally-occurring or non-naturally occurring changes in the encoding nucleic acid or the transcription or regulatory sequences, or due to a defect in a transcriptional cascade that normally leads to Parkin production in a cell. It will be readily appreciated by the ordinarily skilled artisan that "parkin " as used herein also refers to homologs or orthologs of the parkin gene detailed in the examples herein, such that the invention contemplates non-mammalian animals having a defect in a homolog of the parkin gene in that animal.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Overview

The invention is based on the discovery that a non-mammalian animal model having a defective parkin gene and a defect in at least one other gene (e.g., as a result of transposon insertion) can be used to identify gene products that affect a Parkinson's disease (PD) phenotype. Loss-of-function mutations of the parkin gene, which encodes an ubiquitin-protein ligase, are a common cause of Autosomal Recessive Juvenile Parkinsonism (AR-JP).

The inventors have discovered, using the non-mammalian model described herein, as well as by examining transcriptional alterations that occur during muscle degeneration, that oxidative stress response components are induced in parkin mutants and that loss-of-function mutations in oxidative stress components enhance the parkin mutant phenotypes. As such, the results show that oxidative stress or immune system activation play an important role in the etiology of AR-JP.

Non-Mammalian Animal Models and Methods for Producing the Same

The subject invention provides a non-mammalian animal model for Parkinson's disease that includes a non-functional parkin gene and a non-functional mutation in at least one other gene. In some embodiments the gene is a glutathione S-transferase S1 gene. In certain embodiments, the animal model is an invertebrate animal. In further embodiments, the invertebrate animal is a member of the family Drosophilidae. In further embodiments the invertebrate animal is a *Drosophila melanogaster*.

The subject knock-out animal models can be prepared using any convenient protocol that provides for a defect (e.g., a mutation) in at least one gene other than the parkin gene (a "non-parkin gene"). The animals can be either heterozygous or homozygous for the parkin gene defect, the defect in the non-parkin gene, or both. The invention also contemplates animal models having a parkin gene defect (which may be homozygous or heterozygous) and at least one, two, three, four, or five or more non-parkin gene defects (for each of which the animal may be homozygous or heterozygous). In some embodiments, the animal contains a conditionally defective non-parkin gene, in which the absence of or exposure to the condition modulates the production of a defective gene product (e.g., the presence or absence of a drug that affects transcription and/or translation of the gene product of the non-parkin gene)

Methods of producing a non-mammalian animal model, such as *Drosophila melanogaster*, are described in Greene et al., 2003, the entire disclosure of which is incorporated herein by reference. Accordingly the animal models described in Greene et al., (2003) are suitable for use in the subject methods for generating animal models with a mutation in at least one gene other than the parkin gene. Methods of mutating genes in addition to the parkin gene and carrying out enhancer/suppressor analyses are well known to those of skill in the art (Hays, T S et al., Molecular and Cellular Biology (March 1989) 9(3):875-84; Deuring, R; Robertson, B; Prout, M; and Fuller, M T. Mol. Cell. Biol., 1989 9:875-84; Fuller, M T et al., Cell Mot. Cyto. (1989) 14:128-35; Rottgen G, Wagner T, Hinz U Mol. Gen. Genet. 1998 257:442-51).

In some embodiments, the mutation is generated by random P element transposon integration is with the use of transposase. In such embodiments, the mutation in at least one other gene is introduced into the cell(s) within a vector that includes the requisite P element, terminal 31 base pair inverted repeats. Where the cell into which the mutation is to be introduced does not comprise an endogenous transposase, a vector encoding a transposase is also introduced into the cell, e.g. a helper plasmid comprising a transposase gene, such as pTURBO (as disclosed in Steller & Pirrotta, "P Transposons Controlled by the Heat Shock Promoter," Mol. Cell. Biol. (1986) 6:1640-1649). Methods of random integration of transposable elements into the genome of a target *Drosophila melanogaster* cell(s) are disclosed in U.S. Pat. No. 4,670,388, the disclosure of which is herein incorporated by reference.

The above strategy is employed to obtain fertilized eggs that comprise a nonfunctional parkin gene and a mutation in at least one other gene. Generally, the fertilized eggs are allowed to mature under conditions that give rise to the Parkinson's disease phenotype.

Utility

The subject non-mammalian animal models find use in a variety of applications, including: as tools to identify genes and gene products involved in Parkinson's disease; as a screening tool that identifies therapeutic compounds for use in the treatment of Parkinson's disease (e.g. as animal models for human Parkinson's disease); and as tools for use in the identification Parkinson's disease gene targets, i.e. genes whose expression can be modulated, e.g. enhanced or disrupted, in order to alleviate a Parkinson's disease condition. The subject non-mammalian animal models find particular use in screening methods designed to identify therapeutic agents for use in the treatment of Parkinson's disease.

Screening Methods

As mentioned above, the subject non-mammalian animal models find particular utility in screening assays designed to identify compounds or therapeutic target genes that modulate cellular neurodegenerative disorders, particularly Parkinson's disease, with compounds that mitigate one or more symptoms of the disease being of particular interest. Accordingly, the present invention provides a method for screening for an agent that modulates a Parkinson's disease phenotype, including administering an agent to a non-mammalian animal model having a non-functional mutant parkin gene and a defect in at least one other gene (a "non-parkin gene"), and evaluating the non-mammalian animal model for a Parkinson's disease phenotype, wherein a change in the Parkinson's disease phenotype in the non-mammalian animal model in the presence of the agent as compared to a non-mammalian in the absence of the agent indicates that the agent modulates the Parkinson's disease phenotype. In some embodiments, the modulating results in enhancing the Parkinson's disease phenotype. In other embodiments, the modulating results in suppressing the Parkinson's disease phenotype.

Through use of the subject non-mammalian animal models (or cells derived therefrom depending on the particular screening assay), one can identify compounds that have activity with respect to Parkinson's disease. Compounds have activity with respect to a Parkinson's disease if they modulate or have an effect on at least one parameter or symptom of the disease, such as a decrease in dopaminergic neuronal cell death, where the modulatory activity may be to reduce or enhance the magnitude of the symptom, depending on the nature of the disease and the symptom. The Parkinson's disease phenotype includes viability of progeny, the climbing capability of the non-mammalian animal model, the flight capability of the non-mammalian animal model, and the like.

Thus, the screening methods of subject invention can be used to identify compounds that modulate the progression of Parkinson's disease, e.g. by binding to, modulating, enhancing or repressing the activity of a protein or peptide involved in the progression of the Parkinson's disease, and/or compounds that ameliorate, alleviate or even remove the phenotypic symptoms of the disease, where such activity may or may not be the result of activity with respect to the underlying mechanism of the disease.

Screening to determine drugs that lack effect on Parkinson's disease is also of interest. Assays of the invention make it possible to identify compounds which ultimately: (1) have a positive affect with respect to Parkinson's disease and as such are therapeutics, e.g. agents which arrest or reverse Parkinson's disease or ameliorate or alleviate the symptoms of such a condition; or (2) have an adverse affect with respect to Parkinson's disease and as such should be avoided as therapeutic agents.

In some embodiments the assay involves identifying agents that enhance activity of a gene product of a glutathione S-transferase gene. Accordingly the invention provides a method for screening for an agent that increases the level of glutathione S-transferase (GST) or otherwise enhancing GST activity. Such agents include, for example, compounds that increase expression of GST, compound that inhibits or prevents clearance of GST, and the like.

In general such methods involve administering an agent to a non-mammalian animal model having a non-functional mutant parkin gene and a mutant glutathione S-transferase gene, particularly a mutant glutathione S-transferase S1 gene, and evaluating the non-mammalian animal model for a Parkinson's disease phenotype, wherein a change in the Parkinson's disease phenotype in the non-mammalian animal model in the presence of the agent as compared to a non-mammalian in the absence of the agent indicates that the agent increases the level of glutathione S-transferase.

In the screening methods of the subject invention, a quantity of a candidate agent is generally administered to the fly, e.g., by oral administration. Following administration, the effect of the candidate agent on the Parkinson's disease phenotype (or appearance thereof) of the non-mammalian animal model is determined, typically by comparison with a control (e.g., a non-mammalian animal model to which the candidate agent has not been administered). The effect of the candidate agent is determined by determining whether one or more of the phenotypic characteristics of Parkinson's disease are exacerbated or ameliorated in the test non-mammalian animal model as compared to the control non-mammalian animal model, where characteristics that are monitored include viability of progeny, the climbing capability of the non-mammalian animal model, the flight capability of the non-mammalian animal model, and the like, as further described in detail in the examples section below.

The Parkinson's disease phenotype can also be evaluated by examining the death rate of dopaminergic neurons in the subject non-mammalian animal models. Such evaluations can be carried in test animals that have been administered the candidate agent and the results compared to control animal models that have not been administered the candidate agent. The death rate of dopaminergic neurons can be evaluated by, for example, using anti-tyrosine hydroxylase (anti-TH) antiserum in situ. In an exemplary method, aged adult heads may be dissected in cold phosphate buffered saline (PBS) and isolated CNS fixed in 4% paraformaldehyde/PBS. The samples are then washed in PBS 0.1% Triton-X-100, and blocked for approximately 1 hour in 0.1 M Tris-Cl pH 7.5, 0.15 M NaCl, 0.1% Triton-X-100, 10% heat inactivated fetal bovine serum. Anti-TH is then incubated in blocking solution (1:100) at 4° C. overnight. Following washing and incubation of fluorescent secondary antiserum, samples are again washed and mounted between two fine glass coverslips using ProLong antifade medium (Molecular Probes). This preparation allows analysis of the samples from either side to provide the best visualization of all neuron clusters regardless of sample orientation.

The candidate agent is generally administered (e.g., orally) to the non-mammalian animal model. Oral administration can be accomplished by mixing the agent into the non-mammalian animal model, such as a fly, nutrient medium, e.g. water, aqueous solution with additional nutrient agents, etc., and placing the medium in the presence of the fly, (either the larva or adult fly, usually the adult fly) such that the fly feeds on the medium.

Generally a plurality of assay mixtures are performed in parallel with different agent concentrations to obtain a differential response to the various concentrations of candidate agent. Typically, one of these concentrations serves as a negative control, i.e. no compound. In a preferred embodiment, a high throughput screening protocol is employed, in which a large number of candidate agents are tested in parallel using a large number of flies. By "large number" is meant a plurality, where plurality means at least 10 to 50, usually at least 100, and more usually at least 1000, where the number of may be 10,000 or 50,000 or more, but in many instances will not exceed 5000.

Of particular interest in certain embodiments is the use of the subject flies in a high throughput toxicity screening assays. In such high throughput screening (HTS) assays, a plurality of different compound compositions, usually at least 10 different compound compositions, are simultaneously assayed for their activity, if any. Each compound composition in the plurality is assayed for activity by contacting it with a population of the subject non-mammalian animal models having a Parkinson's disease phenotype and determining the effect of the compound composition on the animals. Such HTS methods find particular use in finding agents for use in the treatment of neurodegenerative diseases, e.g. Parkinson's diseases, as only those compounds that treat the disease and yet are sufficiently non-toxic to allow the animal to live are identified as positives for further study.

The subject methods find use in the screening of a variety of different potentially therapeutic candidate agents. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Candidate agents having therapeutic activity with respect to Parkinson's disease can be identified based on their ability to at least ameliorate, if not completely alleviate or remove, one or more of the phenotypes of the adult non-mammalian animal models of the subject invention, such as dopaminergic neuron survival, viability flight capability, climbing capability, sensitivity to chemical stress and the like, as described above and in the examples section below.

The above screening methods may be part of a multi-step screening process of evaluating candidate therapeutic agents for their efficacy (and safety) in the treatment of Parkinson's diseases in mammalian hosts, e.g. humans. In multi-step screening processes of the subject invention, a candidate compound or library of compounds is subjected to screening in a second in vivo model, e.g. a mouse model, following screening in the subject non-mammalian animal model. Following the initial screening in the non-mammalian animal models of the subject invention, the positive compounds are then screened in non-human mammalian animal models, including non-human mammalian animal models. In addition, a pre in vivo screening step may be employed, in which the compound is first subjected to an in vitro screening assay for its potential as a therapeutic agent in the treatment of Parkinson's disease. Any convenient in vitro screening assay may be employed, where a variety of suitable in vitro screening assays are known to those of skill in the art.

Identification of Gene Targets

In addition to their use as animal models for screening candidate therapeutic agents, the subject flies also find use in the identification of Parkinson's disease gene targets, i.e. genes whose expression or activity can be beneficially modulated to treat Parkinson's diseases. Genes that have a beneficial effect on the phenotype when their activity is modulated through mutation encode proteins that represent therapeutic targets for the development of compounds that inhibit the function of the protein. Gene based therapies can be identified by doing traditional enhancer/suppressor analyses in the subject flies. In these analyses, genes in the subject flies are mutated to identify ones that either exacerbate or alleviate a Parkinson's disease phenotype. Methods of mutating genes and carrying out enhancer/suppressor analyses are well known to those of skill in the art (Hays, T S et al., Molecular and Cellular Biology (March 1989) 9(3):875-84; Deuring, R; Robertson, B; Prout, M; and Fuller, M T. Mol. Cell. Biol., 1989 9:875-84; Fuller, M T et al., Cell Mot. Cyto. (1989) 14:128-35; Rottgen G, Wagner T, Hinz U Mol. Gen. Genet. 1998 257:442-51).

Accordingly, the invention provides a method for screening for a gene that modulates a Parkinson's disease phenotype, including evaluating a Parkinson's disease phenotype in a non-mammalian animal model having a non-functional mutant parkin gene and a defect in at least one other gene (a "non-parkin gene"), wherein a change in the Parkinson's disease phenotype in the non-mammalian animal model as compared to a control non-mammalian animal model indicates that the gene modulates the Parkinson's disease phenotype. In some embodiments the non-parkin gene is a glutathione S-transferase S1 gene.

In some embodiments, the defect in at least one non-parkin gene is generated by P element transposon insertion. In some embodiments, the Parkinson's disease phenotype includes viability of progeny, the climbing capability of the non-mammalian animal model, the flight capability of the non-mammalian animal model, death rate of dopaminergic neurons, and the like, as described in greater detail in the examples section below. In some embodiments, the modulating results in enhancing the Parkinson's disease phenotype. In other embodiments, the modulating results in suppressing the Parkinson's disease phenotype.

Genes that mutate to enhance the Parkinson's disease phenotype in a loss-of-function manner yield potential protein therapeutics for Parkinson's disease conditions, since elevating the normal gene product level of such genes potentially alleviates the Parkinson's disease condition. Genes that mutate to suppress the Parkinson's disease condition in a loss-of-function manner yield gene targets for disruption to alleviate the Parkinson's disease conditions, where disruption of these genes can be achieved using a variety of methods, ranging from deleting the DNA for the target gene to inhibiting its transcription, translation, or protein activity. For screening candidate agents, small molecule antagonists to these genes can be constructed and evaluated for efficacy in the fly model through oral administration. Alternatively, small molecule antagonists can be identified in high-throughput in vitro or cellular screens for activity of the gene product and validated in the fly model. Alternatively, the human homolog of the gene can be identified and small molecular antagonists that inhibit the gene product of the human homolog can be identified in high-throughput in vitro or cellular screens and validated in rodent models of PD. Alternatively, large molecular antagonists can be delivered by gene therapy, as described infra.

Kits

Also provided by the subject invention are kits for use in performing the subject screening methods. The subject kits include at least a plurality of non-mammalian animal models of the subject invention, or a means for producing such a plurality of flies, e.g. a male and female fly of the subject invention, vectors carrying requisite genes, such as a transgene, a transposase gene, GAL4, etc. The flies may be housed in appropriate container(s), e.g. vials. The subject kits may also comprise a nutrient medium for the animals, e.g. *drosophila* medium.

Therapeutic Agents and Pharmaceutical Compositions

Also provided by the subject invention are therapeutic agents for use in treating a neurodegenerative condition, as well as pharmaceutical formulations thereof. The therapeutic agents of the subject invention are those agents identified using the screening methods described supra that show beneficial activity with respect to a neurodegenerative condition (or agents known to have an effect on the expression of a gene identified as modulating the phenotype of a neurodegenerative condition, where identification employs the use of the subject non-mammalian animal models).

Also provided are pharmaceutical compositions of the subject therapeutic agents. In the pharmaceutical compositions or formulations of the subject invention, agents described above are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof (as identified using the mutant screen analysis protocols described supra), it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Molecular Genetics

DNA sequences encoding the *Drosophila* parkin ortholog were identified by searching the Berkeley *Drosophila* Genome Project Database (available on the worldwide web at fruitfly.org/blast) using a human Parkin polypeptide query sequence (NP_004553). A cDNA clone identified from this analysis (SD01679) was fully sequenced and this sequence was compared with the corresponding genomic DNA sequence to identify splice junctions in the parkin gene. The predicted Parkin polypeptide sequence was aligned to human Parkin by using the CLUSTALW algorithm.

Parkin mutants were generated by inducing transposition of the EP(3)3515 P element insertion using an established procedure (available on the worldwide web at engels.genetics.wisc.edu/Pelements/index.html). To identify P element insertions in parkin, genomic DNA was obtained from the offspring of approximately 5,500 flies and subjected to multiplex PCR analysis with a primer specific to the P element terminal repeat sequence and a pool of primers corresponding to sequences within the parkin gene. This analysis led to the recovery of a single line, park$^{EP(3)LA1}$, bearing an insertion of 71 basepairs (bp) upstream of the parkin start codon. This chromosome was used to generate imprecise excision alleles of parkin by using standard procedures (Engels et al., Cell, 62:515-525 (1999)). Deletion breakpoints of the imprecise excision alleles were determined by sequencing. Ethyl methanesulfonate alleles of parkin were identified by screening a collection of homozygous viable male sterile stocks, previously identified by B. Wakimoto, D. Lindsley, and C. Herrera, from a collection established by E. Koundakjian, R. Hardy, and D. Cowen in the laboratory of C. Zuker (Tsunoda et al., Nature, 388:243-249 (1997)), for failure to complement the park$^{25}$ allele.

The parkin cDNA clone SD01679 was used to generate transgenic lines after altering a nucleotide sequence polymorphism at codon 240 of this cDNA to correspond to the parkin amino acid sequence predicted from sequence deposited in the Berkeley *Drosophila* Genome Project database and consistent with our laboratory strains. The parkin coding sequence from this modified cDNA was amplified by using PCR primers bearing sequence changes designed to improve translation, and to introduce restriction sites for cloning purposes. The product was ligated into the P{UAST} vector (Tsunoda et al., 1997), sequenced to ensure the integrity of the parkin coding sequence, and introduced into the *Drosophila* germ line by using standard procedures.

Northern blot analysis was performed by using 1.5 μg poly(A)$^+$ RNA (Clontech) per lane with standard procedures.

Genetic Screen

The EP collection was obtained from Exelixis. Initial screening crosses were carried out in polystyrene vials using standard food. Repetition of results was carried out in glass vials. All crosses were carried out at 25° C. For the 2$^{nd}$ chromosome EP lines, 2-3 males from each EP stock were mated to 3-4 females from the marked parkin stock in the F1 cross. For the F2 cross, 3-4 males of the appropriate genotype were mated to 5-6 females of the 24B-GAL4, parkin stock. These crosses were placed at 25° C. 12 days after the F2 cross was set up, the vials were cleared. Flies were allowed to eclose for 4 days, then collected and counted. Parkin mutant flies recovered from these crosses were also examined qualitatively for droopy wing posture and general movement ability.

For the X chromosome stocks, 3-4 virgin females were collected from each of the EP stocks and crossed to 2-3 males bearing the marked parkin allele. Appropriate male progeny from this cross were then set up in the F2 cross as described for the 2$^{nd}$ chromosome screen. Only the female progeny from the F2 cross carried the EP element and were included in the ratio calculations. Male F2 progeny from these crosses were examined to control for the viability of parkin mutants under the conditions used for these crosses.

Electron Microscopy

Tissues for electron microscopy were prepared by dissecting aged pupae in 2% paraformaldehyde, 2.5% gluteraldehyde and fixing overnight. After rinsing in 0.1 M cacodylate buffer with 1% tannic acid, samples were post-fixed in 1:1 2% OsO$_4$ and 0.2 M cacodylate buffer for 1 hr. Samples were rinsed, dehydrated in an ethanol series and embedded using Epon.

Tissue Preparation for Array Analysis

Pupae were collected at the white prepupal stage and allowed to age for 48 hours at 25° C. The pupae were then frozen in liquid nitrogen and stored at −80° C. until use. Total RNA was extracted from the appropriate tissue, either from 30 flies or 35-40 aged pupae per RNA prep using Trizol Reagent (Invitrogen). 3-4 independent RNA samples of mutants and controls were prepared.

Array Analysis

30 μg total RNA was oligo dT primed and first strand cDNA synthesized in the presence of amino-allyl dUTP. Cy3 or Cy5 was coupled to these strands and the reactions were quenched with 4M hydroxylamine, combined and the labeled strands purified using Qiagen PCR purification kit. Labeled control and mutant samples were then hybridized together to chips containing either approximately 6,000 (1-day old flies) or 12,000 (48 hour pupae) spotted *Drosophila* cDNAs (*Drosophila* Gene Collection 1 and *Drosophila* Gene Collections 1 and 2, respectively). After washing, the arrays were scanned.

GenePix Pro 3.0 software was used to analyze the scanned files including flagging of bad or missing spots. Background-subtracted intensities were calculated for all spots. Ratios of fluorescence intensity were normalized in an intensity-dependent manner using loess smoothing to correct for nonlinearity (Yang et al, Nucleic Acids Res. Feb. 15, 2002; 30(4):e15). A total of 6-8 microarrays were used for each experiment, including dye swapping within each sample pair. Dye swap values were averaged within an RNA prep prior to statistical analysis. The normalized ratios for each experiment were then input into the Cyber T algorithm (P. Baldi and A.D. Long, Bioinformatics, 17, 6, 509-519, (2001)) which determines which spots have ratios that differ significantly from the mean using Bayesian statistics. False discovery rates (significance of the change) were assigned using a method that is independent of the fold change in expression of the transcript (Benjamini and Hochberg *Journal of the Royal Statistical Society. Series B (Methodological)*, Volume 57, Issue 1 (1995), 289-300). A false-positive rate of 1% was used for the results described.

Slot Blot Analysis

Total RNA samples were prepared as described above. 3 μg total RNA for either control or mutant samples were loaded into slots on a Bio-Dot SF Microfiltration apparatus (Bio-Rad) and transferred to Hybond-N membrane. Probes were generated by digoxigenin-incorporation (Invitrogen) in an in vitro transcription reaction using cDNAs from the array as templates and hybridized to membrane using standard techniques. Probes were detected using AP-conjugated anti-Dig and CDP-star luminescence reagent. Signal intensity was captured and quantified using Labworks software on a UVP. A minimum 6 spots were used for the intensity calculation for each probe used. The data was calculated as a ratio of signal intensity of the gene of interest to a control whose transcript level is not altered on the array for both parkin mutant (park25 homozygous) and control (parkrvA homozygous) RNA samples. The mean and standard deviation of the ratios was computed for each gene analyzed in both park- and control samples.

Antibody Generation

The antiserum used to detect *Drosophila* Parkin was generated by expressing 6X-HIS-tagged recombinant Parkin using the Pet11a vector system (Novagen). Recombinant protein was dissolved in urea buffer and purified over a Ni-NTA beads (Qiagen) using standard procedures. This protein was used to inoculate rabbits to generate serum (R&R Rabbitry, Stanwood, Wash.) using standard procedures.

RNAi in Cell Culture

*Drosophila* S2 cells were maintained in culture at room temperature. Double stranded RNA against parkin was synthesized using the Megascript RNAi kit (Ambion). 15 μg of dsRNA was added to cells and incubated for 4 days before harvesting. Cells were lysed and mixed with 2× protein sample buffer for western analysis.

Western Blot Analysis

Tissues were homogenized in protein sample buffer, electrophoresed through 4-20% polyacrylamide gels and transferred to nitrocellulose membrane using standard techniques. Blots were probed with anti-cyclin E 1:50 (Richardson et al., Development 121(10):3371-9 (1995)), anti-ADH (Brogna and Ashburner, Embo J. 16, 2023-31 (1997)) 1:20,000, or anti-Parkin (see above) 1:10,000. Blots were developed using HRP-conjugated secondary antibodies (Bio-Rad) and Western Lightning chemiluminesence reagent.

Genetic Analysis

Available mutations were identified and crossed into the park25 mutant background using standard techniques. Heterozygous flies bearing the mutation of interest and the park25 allele were crossed together and the resulting progeny were counted to determine the number of heterozygotes and homozygotes. In the case that the mutation of interest was not homozygous viable, flies that were heterozygous for this mutation and homozygous for park25 were counted for the assays.

Behavioral Assays

Longevity assays were conducted at 25° C. Flies (0-24 hour old) were collected and transferred to new vials every 2-3 days. The number of dead flies was recorded when transferring. Longevity experiments were performed in triplicate for each genotype. Statistical significance was calculated with a two-tailed Mann-Whitney test.

Flight tests were performed by using an apparatus described by Benzer (Sci. Am., 229:24-37 (1973)) with minor modifications. An acetate sheet was divided into five equal parts, coated with vacuum grease, and inserted into a 1-liter graduated cylinder. To perform flight tests, 1- to 2-day-old flies were dispensed into the apparatus by gently tapping vials containing 20 flies into a funnel placed on top of the graduated cylinder. Flies became stuck to the sheet where they alighted. The sheet was removed and the number of flies was counted in each of the five regions. The flight index was calculated as the weighted average of the region into which the flies landed divided by four times the number of flies in the assay. At least 100 flies of each genotype were tested.

Climbing assays were performed by using a countercurrent apparatus developed initially for phototaxis experiments (Benzer, PNAS, 58:1112-1119 (1967)). Twenty to thirty flies were placed into the first chamber, tapped to the bottom, then given 30 sec to climb a distance of 10 cm. Flies that successfully climbed 10 cm or beyond in 30 sec were then shifted to a new chamber, and both sets of flies were given another opportunity to climb the 10-cm distance. This procedure was repeated a total of five times. After five trials, the number of flies in each chamber were counted. The climbing index was calculated in the same manner as the flight index (see above). At least 60 flies were used for each genotype tested.

Analysis of DA Neurons

DA neurons were analyzed in situ using anti-tyrosine hydroxylase (anti-TH) antiserum Ab152 (Chemicon). Aged adult heads were dissected in cold phosphate buffered saline (PBS) and isolated CNS fixed in 4% paraformaldehyde/PBS for 30 min. Samples were washed in PBS 0.1% Triton-X-100, and blocked for 1 hour in 0.1M Tris-Cl pH 7.5, 0.15M NaCl, 0.1% Triton-X-100, 10% heat inactivated fetal bovine serum. Anti-TH was incubated in blocking solution (1:100) at 4° C. overnight. Following washing and incubation of fluorescent secondary antiserum, samples were again washed and mounted between two fine glass coverslips using ProLong antifade medium (Molecular Probes). This preparation allows analysis of the samples from either side to provide the best visualization of all neuron clusters regardless of sample orientation.

Example 1

Transcriptional Profile of 1-Day Old Parkin Mutants

To examine the differences between parkin mutants and controls at the transcriptional level, expression analysis was performed on whole 1-day-old adult flies using cDNA microarrays. This time point was chosen as 1-day-old parkin mutants show clear phenotypes including muscle degeneration, indicating that transcriptional differences between parkin mutants and controls are likely present. The microarrays used for these experiments contain approximately 6,000 spotted *Drosophila* cDNAs (*Drosophila* Gene Collection 1); about 45% of the predicted genes in the genome. Control and mutant RNAs were labeled, hybridized to the chips, and the ratio of the signals was determined for each spot. After normalization, the Cyber T algorithm (available on the worldwide web at visitor.ics.uci.edu/genex/cybert/) was used to identify any spots with significantly altered expression (altered intensity ratios) in parkin mutants relative to controls.

At a false discovery rate of 1% there were approximately 1,000 genes with altered expression in 1-day-old parkin mutants relative to controls, representing about ⅙ of the genes on the chip. Among this large group of altered transcripts, approximately half of the transcripts were decreased in parkin mutants relative to controls and approximately half were increased, though the magnitudes of change for the decreased transcripts was greater. The genes whose transcripts were altered in 1-day-old parkin mutants fell into many categories, and analysis of the biological process gene ontology terms for these altered transcripts reveals alterations in many different processes in parkin mutants. There are 700 different biological process categories represented among the genes altered in 1-day-old parkin mutants, and this is 44% of all annotated biological processes for *Drosophila*. As the large number of changes seen implies that this time point may be too late in the degenerative process to capture events that initiate pathology, another set of experiments was initiated to examine the transcriptional profile of an earlier stage in development.

Example 2

Characterization of Muscle Degeneration in Parkin Mutant Pupae

Prior to proceeding with further transcriptional profiling experiments, it was necessary to establish a stage early in the time course of muscle degeneration to minimize downstream effects. To determine an appropriate time point, parkin mutant pupal flight muscles were examined by transmission electron microscopy (TEM). TEM sections were taken of the indirect flight muscle of parkin mutants and controls at various time points after puparium formation (APF). As previously reported, 96 hour pupal flight muscles display mild mitochondrial pathology. However, at 48 hour APF, the morphology of mutant flight muscles were indistinguishable from controls in terms of morphology of the developing myofibrils, and the mitochondrial integrity of parkin mutants appeared identical to that of controls. The overall structure and size of the mitochondria, as well as the structures of the cristae, are indistinguishable between parkin mutants and controls. Based on the morphological similarity, transcriptional differences between mutants and controls at this time point likely represent an early response to loss of parkin function. Thus, further transcriptional profiles were obtained using this time point.

Example 3

Transcriptional Profile of 48h Parkin Mutant Pupae

RNA was extracted from 48h parkin mutant and control pupae and hybridized to larger cDNA arrays containing approximately 12,000 cDNA spots (*Drosophila* Gene Collections 1 and 2). This represents a large portion of the number of predicted genes in the genome, which is approximately 14,000. The hybridizations and statistics were carried out in the same manner as for the 1-day-old adult time point, and for this analysis, a false discovery rate of 1% was also used. 26 genes showed altered expression in parkin mutants relative to controls, and these are shown in Table 1A and 1B.

TABLE 1A

Genes up-regulated in parkin mutant pupae[1]

| cDNA | gene | Function | fold expression change |
|---|---|---|---|
| Immune related | | | |
| RH02253 | Dpt | antibacterial humoral response | 3.8 |
| RH25931 | IM4 | immune induced molecule | 3.6 |
| LD44267 | CG1105 | immunoglobulin | 3.4 |
| LP07339 | LysE | lysozyme, antibacterial response | 3.3 |
| LP06719 | LysS | lysozyme, antibacterial response | 2.5 |
| LP05763 | AttA | antibacterial humoral response | 2.2 |
| Oxidative damage and electron transport | | | |
| LD37279 | CG8032 | oxidoreductase activity | 2.6 |
| RE65105 | Cyp6a23 | cytochrome P450 electron transport | 2.5 |
| GH14654 | GSTE1 | glutathione transferase | 2.2 |
| GH02075 | CG2789 | mitochondrial transporter | 1.9 |
| Other | | | |
| RH55416 | CG32758 | RA, PDZ, PX domains | 3.9 |
| LD41905 | CG12505 | Zn finger | 3.3 |
| LD40495 | CG5384 | ubiquitin hydrolase activity | 3.2 |
| LD44305 | CG8223 | tetratricopeptide repeat | 3.2 |
| LP04037 | CG3604 | trypsin inhibitor like | 2.9 |
| RE58815 | ImpL3 | lactate dehydrogenase | 2.6 |
| LD44053 | Doa | kinase activity | 2.5 |
| RH26422 | CG7418 | unknown | 2.3 |
| AT13773 | scpr-A | contains PR-1-like domain | 2.1 |
| RE25329 | Dgp-1 | translation elongation factor | 1.9 |
| LD12965 | Map205 | microtubule binding | 1.8 |

[1]At a false discovery rate of 1%

TABLE 1B

Genes down-regulated in parkin mutant pupae[1]

| cDNA | gene | Function | fold expression change |
|---|---|---|---|
| GH15170 | CG11459 | cysteine protease | −2.3 |
| LP06769 | TotB | humoral defense | −2.2 |
| RE11385 | CG13822 | unknown | −2.1 |
| HL08023 | CG1561 | unknown | −1.9 |
| GH15921 | CG16820 | ribosomal protein L30p | −1.9 |

[1]At a false discovery rate of 1%

The majority of genes showing altered expression in parkin mutants were up-regulated relative to controls. These up-regulated genes could be grouped into two categories including immune-response related (6 genes) or oxidative and electron-transport related (4 genes). The remaining 11 up-regulated genes and the 5 down-regulated genes could not be grouped into a specific category or are of unknown function.

To validate the pupal array findings, the alterations in transcript levels were verified for several of the genes found to be altered in parkin mutants. To do this, slot blot analysis was performed using RNA from parkin mutant and control pupae. Equal amounts of total RNA were loaded and probed with labeled probes corresponding to the gene of interest. Signal was quantified in both parkin mutants and controls and shown in FIG. 1. Good correlation was seen between the difference in transcript levels predicted by the array and that observed using the slot blot apparatus shows that the results from the array likely represent actual differences in transcript abundance.

Figure 2:
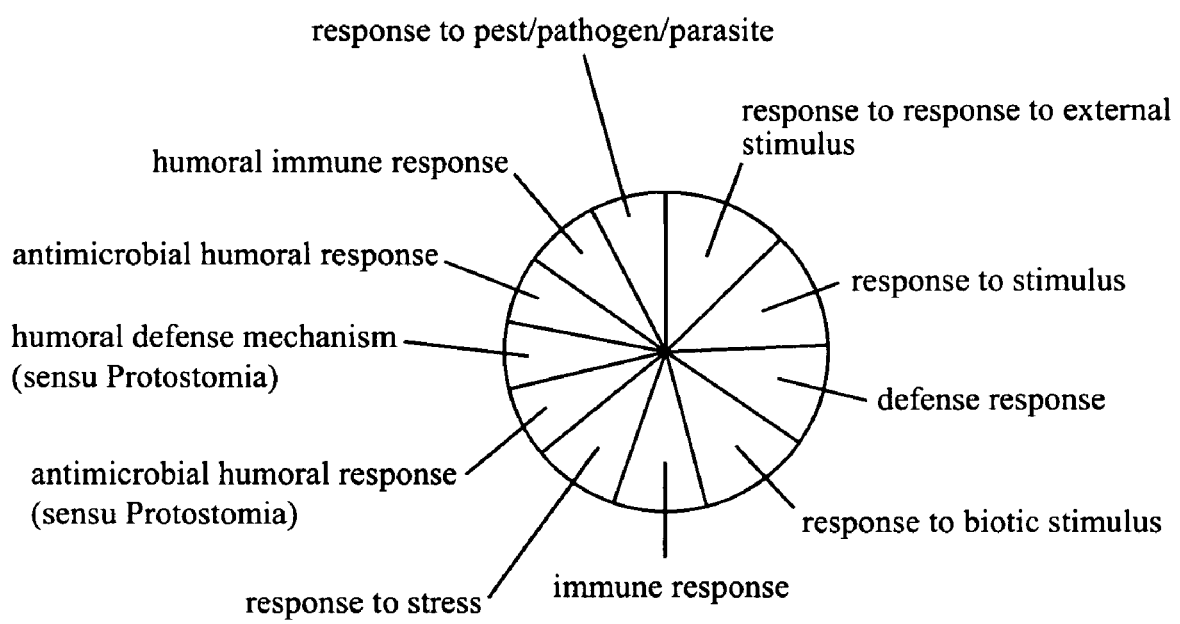
FIG. 2 shows gene ontology categories for up-regulated genes in parkin mutant pupae.

To systematically identify which pathways and processes are altered in parkin mutant pupae, the EASE program was used to categorize the altered transcripts. The EASE program can be used to identify gene ontology categories that are significantly over-represented among the transcripts that are altered in abundance. In the case of parkin mutants, at a 1% false discovery rate, the most changed category of up-regulated transcripts is that of the immune and defense response, followed by oxidative stress response. The down-regulated transcripts fail to be grouped into any significant category. If the false discovery rate is increased to 5%, the transcripts altered fall into the pathways and processes shown in FIG. 2. These same categories are seen if the false discovery rate is increased further to 10%, 15% or 20%. No categories are detected for down-regulated transcripts at any of these false discovery rates. If the false discovery rate is increased to 25%, the list of genes identified as being alternatively regulated in parkin mutants increases to about 800 genes, ¼ of which could be false positives. Though the significance of individual genes on this list is not high, this list can also be put through the EASE program to identify trends in gene expression changes. At a 25% FDR, the categories changed for the up-regulated transcripts included the immune response, oxidative stress response and categories related to metabolism of glucose and alcohol. For down-regulated transcripts, functional categories begin to emerge, the most significant of which are mitochondrial processes including mitochondrial ribosomes and other mitochondrial function and biosynthetic activity. This shows that, despite the lack of visible alterations in the mitochondria at this time point, there may be early changes taking place.

Mitochondrial dysfunction is a prominent feature of the muscle pathology in Drosophila parkin mutants. Dysfunctional mitochondria are likely a source of oxidative stress as they are more likely to produce damaging radicals. It is unclear at this point how the loss of Parkin function leads to the mitochondrial dysfunction. At the 48 hour pupal stage, there are no visible signs of mitochondrial pathology, yet there is up-regulation of oxidative damage response components. This shows that damage to the mitochondria may already be occurring at this time point. One possibility is that Parkin is responsible for degrading oxidatively damaged proteins or damaged mitochondrial components. In the absence of Parkin function, then, these products are allowed to accumulate, resulting in further damage and the onset of mitochondrial dysfunction and degeneration.

Example 4

Analysis of Pathways Previously Implicated in Parkin Pathology

Previous studies of Parkin have implicated its E3 ligase activity in several processes including ER stress and cell cycle regulation. To investigate whether there is evidence for alterations in either of these pathways in Drosophila parkin mutants, the transcriptional profiles generated from both developmental stages were examined to look for changes in components of these pathways.

One hypothesis about the origins of pathology in the absence of Parkin is that cells are mounting an unfolded-protein response and undergoing ER stress. ER stress is associated with a defined transcriptional profile which can be examined in the data obtained from parkin mutants. A comparison was done that examined the Drosophila homologs of 381 yeast genes identified to be up-regulated in response to ER stress of various kinds. Of the 381 yeast genes, 188 had Drosophila homologs with cDNA spots on the array. The median expression ratio from these spots was −1.07, with 81% of these homologs having expression ratios between 1.2 and −1.2, indicating no significant change in transcript levels. In addition, approximately half of these genes showed a slight negative ratio indicating a tendency towards down-regulation. This contrasts with the fact that the genes were identified in the yeast study as being up-regulated in response to ER-stress-inducing treatment. Similar analysis was carried out using the 1-day-old-adult array data, and similar results were seen. In addition, Table 2 depicts several of the key mediators of this pathway and shows that they are not altered in parkin mutants. These results show that there is not activation of the ER stress pathway in the absence of Drosophila parkin.

TABLE 2

Relative expression of ER-stress-associated genes in parkin mutant pupae

| cDNA | Gene | Function | Expression Ratio |
| --- | --- | --- | --- |
| GH01881 | Relish | transcription in NF-kappaB cascade | 1 |
| LD41715 | PERK | ER elongation factor kinase | 1 |
| RH21402 | BiP | ER hsp/chaperone activity | 1.1 |
| GH09250 | Xbp1 | X-box binding transcription factor | −1.2 |
| SD05937 | CrebA | cyclic-AMP response element binding | −1.2 |

Figure 3:
FIG. 3 shows that Cyclin E levels are not changed in parkin mutants or in cells treated with dsRNA against parkin. Panel A shows CyclinE levels in control (+) and parkin mutant (−) 48h pupae, 96h pupae and whole adults. Panel B shows that antiserum raised against recominant *Drosophila* Parkin detects Parkin in extracts from whole flies overexpressing a parkin cDNA (park o/exp) and flies that are wild-type for parkin (park+/+), and wherein this band is not present in extracts from parkin mutants (park−/−). Panel C shows S2 cells treated with dsRNA against an unrelated gene (NPC1a) (control) show parkin protein, which gets drastically reduced in cells treated with dsRNA corresponding to parkin. The band marked with an asterisk is a nonspecific band seen with the parkin antibody. In cells treated with either control or parkin dsRNA, Cyclin E levels remain unchanged. Antiserum to ADH was used as a loading control to show equal protein loading.
Figure 3:
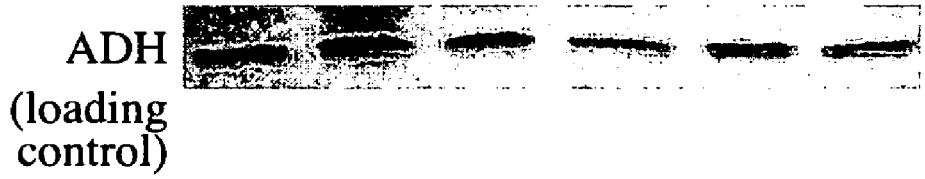
Figure 3:
Figure 3:
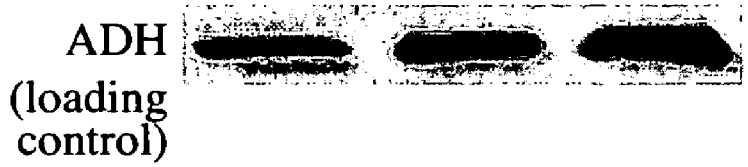
Figure 3:
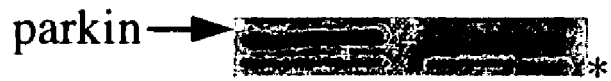
Figure 3:
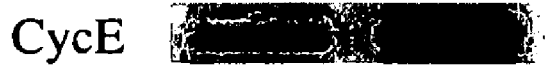
Figure 3:
Figure 4:
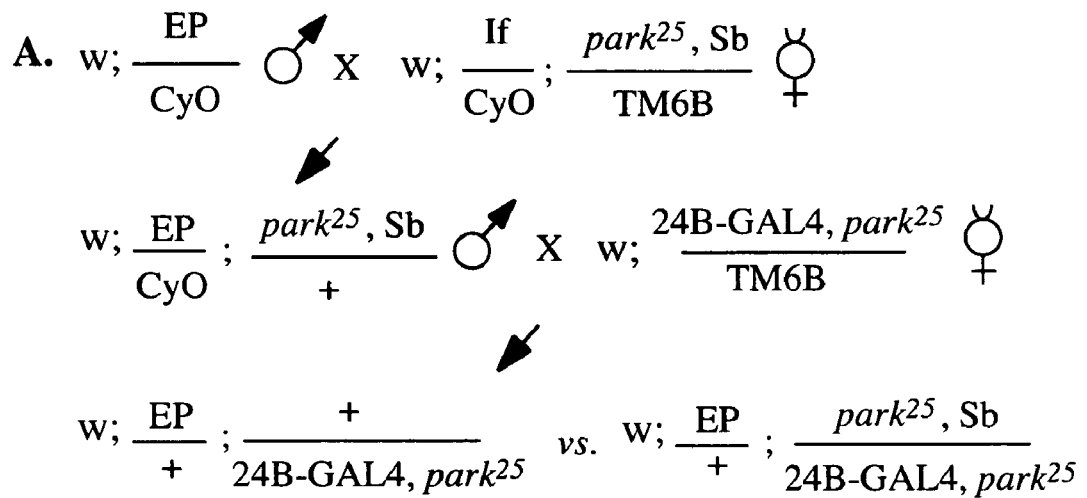
FIG. 4 shows the crossing schemes used in EP screen for parkin modifiers. Panel A shows the crossing scheme used in the 2nd chromosome screen. Panel B shows the crossing scheme used in the X chromosome screen. EP represents the transposon insertion being screened.
Figure 4:
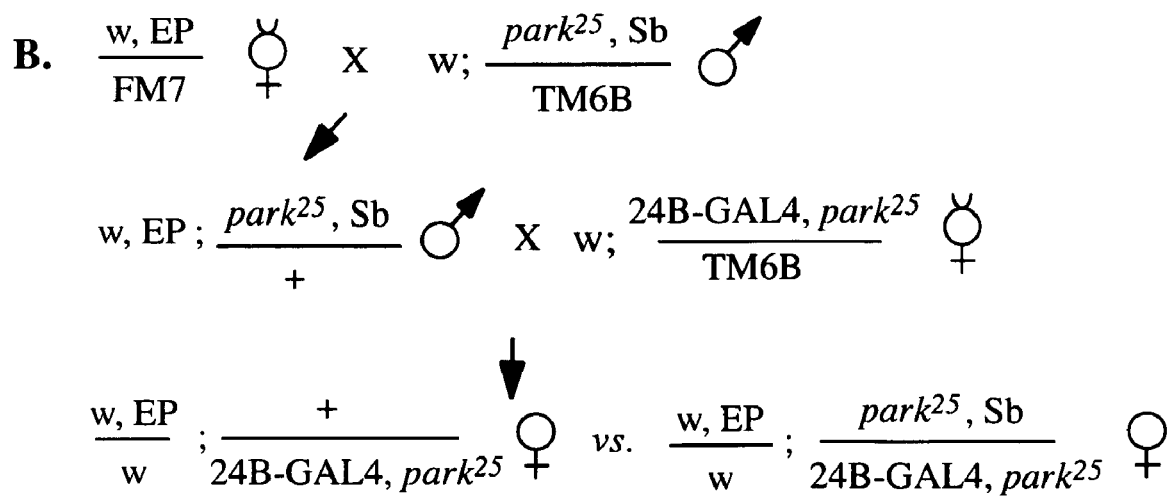

The identification of Cyclin E as a putative Parkin substrate generates an additional hypothesis about pathology in patients with parkin mutations: the inappropriate activation of the cell cycle in postmitotic cells causes apoptosis of these cells. As the regulation of the cell cycle is complicated and dependent on a number of transcriptional and post-transcriptional alterations, a survey of several categories of genes was undertaken. Table 3 depicts many genes involved in cell cycle activation and shows that the average expression of these genes is not changed from controls in parkin mutant pupae. In 1-day old parkin mutant adults, there is evidence for a down-regulation of genes involved in cell cycle, which is the opposite of what would be predicted if cell cycle activation was taking place. Furthermore, Cyclin E has been shown to be a Parkin substrate, and its buildup in the absence of Parkin is hypothesized to cause inappropriate cell cycle activation and subsequent apoptosis. However, in Drosophila parkin mutants, Cyclin E levels are indistinguishable from controls (FIG. 3, Panel A). This is the case in many stages of development, preceding pathology through the 1-day adult stage where pathology is prominent. In addition, cultured *Drosophila* cells that have reduced parkin expression through the use of RNA interference also do not show altered levels of Cyclin E, despite greater than 90% reduction of Parkin protein levels in these cells (FIG. 3, Panels B and C).

TABLE 3

Relative expression of cell-cycle genes in parkin mutant pupae

| cDNA | Gene | function | Expression Ratio |
|---|---|---|---|
| Cyclins | | | |
| LD44443 | CycA | cyclin-dependent kinase factor | 1.1 |
| LD23613 | CycB | cyclin-dependent kinase factor | −1.1 |
| RE64430 | CycB3 | cyclin-dependent kinase factor | 1 |
| LD35705 | CycC | cyclin-dependent kinase factor | −1.1 |
| LD22957 | CycD | cyclin-dependent kinase factor | 1.1 |
| LD17578 | CycE | cyclin-dependent kinase factor | −1.2 |
| SD26182 | CycH | cyclin-dependent kinase factor | 1 |
| DNA metabolism | | | |
| LD25083 | CG5971 | DNA clamp loader | −1.3 |
| GH20028 | CG6204 | DNA helicase in replication | −1.1 |
| LD17208 | CG6701 | DNA helicase in replication | −1 |
| LD24482 | Dref | DNA replication-related element | −1 |
| RE31829 | Rad17 | DNA polymerase processivity factor | −1 |
| HL01263 | skpA | chromosome segregation | −1.1 |
| AT18217 | skpD | chromosome segregation | −1 |

In addition to oxidative-stress-response genes, another category of up-regulated genes in parkin mutant pupae includes genes involved in the innate immune response. The *Drosophila* parkin phenotypes appear to be cell autonomous in that they can be rescued by expression of a parkin transgene specifically in the tissues that are affected. This shows that the induction of immune response components may be a secondary effect. Interestingly, increased immune responses along with induction of oxidative-stress-response genes were shown under conditions of oxidative stress and in studies of aging. This study compared the transcriptional profiles of aged or oxygen-stressed flies and found increased immune response as well as increased levels of stress-response genes under both of these conditions. In addition, studies in *C. elegans* long-lived mutants have also shown induction of anti-oxidative damage genes as well as immune response genes upon aging. These studies show a potential link between these two phenomena as organismal defense mechanisms that are induced to deal with stresses. Interestingly, a glutathione-S-transferase gene that was recently identified through association studies for PD is thought to play a role in the modification of IL-1β, an inflammatory cytokine. This provides a link between oxidative stress and immune system components in the pathogenesis of PD.

One possible mechanism that would give rise to the up-regulation of oxidative stress response elements and the induction of immune response genes is the buildup of nitric oxide (NO). Feeding of NO-inducing compounds to *Drosophila* larvae has been shown to cause an induction of the immune response, particularly the genes Dpt and Drs. Dpt is one of the most highly up-regulated genes in parkin mutant pupae, and if there is a buildup of NO in parkin mutants, the induction of the immune response may be a byproduct of this. Excess NO, especially in the presence of superoxide, can cause the production of highly cytotoxic species, which the cell may respond to by up-regulating oxidative stress response genes. Excess NO could be produced by dysfunctional mitochondria in parkin mutants. In addition, there may be an accumulation of nitrosylated proteins due to NO buildup. Recent studies have shown that in mammals, Parkin itself can be nitrosylated and that this can modulate its ubiquitin E3 ligase activity.

The transcriptional profile data was also used to look for evidence of involvement of other hypothesized pathways in parkin pathology. One hypothesis about the role of Parkin in the cell is that it plays a role in preventing induction of the unfolded protein response/ER stress response. If this is the case, it would be expected that this pathway would be up-regulated in parkin mutants. Analysis of transcriptional profile data from parkin mutant pupae shows that signature genes associated with this response are not altered in their transcript levels, implying that this pathway is not active. Further, comparison of a large list of genes identified from yeast studies of the unfolded protein response also provides no evidence that the ER stress pathway is activated.

Additionally, there was no evidence found for cell cycle activation in either the pupal or adult stage of *Drosophila* parkin mutants. In fact, there is evidence for down-regulation of the cell cycle components in 1-day-old parkin mutants vs. controls. Furthermore, the absence of alteration of levels of Cyclin E, a proposed Parkin substrate and cell cycle inducer, in parkin mutants suggests that there is no cell cycle activation in this model. Both the ER stress and cell cycle pathways are linked to Parkin through the identification of proposed Parkin substrates. The fact that they are not altered in parkin mutants, even though parkin mutants show pathology in several tissues shows that these pathways are not playing a causative role in parkin pathogenesis.

Example 5

Genetic Interactions Between Parkin and Array-Identified Genes

To test the functional significance of genes identified in the array analysis, genetic interactions between parkin and the genes whose transcripts are altered in parkin mutants were examined. To perform this analysis, the parkin phenotype of partial pupal lethality was used: in a cross of parkin heterozygotes under standard laboratory conditions, only approximately 75% of the expected Mendelian numbers of flies are observed. Thus, in the absence of any modification, approximately 25% of flies eclosing from a cross of parkin heterozygotes are homozygous parkin mutants. The differs from the expected Mendelian ratio for this cross, which would be 33% as the balancer chromosome that segregates opposite of parkin alleles is not homozygous viable.

Figure 5:
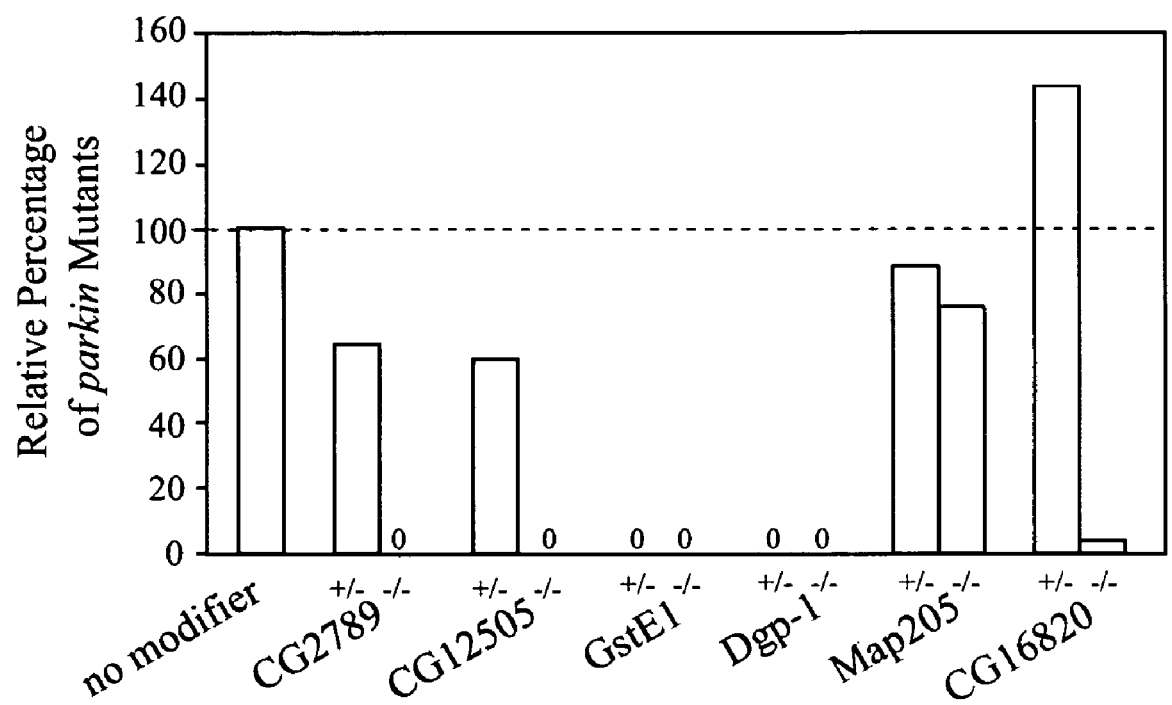
FIG. 5 shows results of genetic interactions between parkin and array-identified genes. Shown are percentages of parkin mutants of total flies eclosing in either a heterozygous or homozygous array-gene allele background. The percentage of parkin mutants in the absence of other alleles is set to 100%. All array-identified alleles used in the analysis produced near expected numbers (between 85-100%) of homozygous progeny from a cross of heterozygotes in a wild-type parkin background, indicating that the reduction in viability seen using these alleles in parkin mutants is a results from a genetic interaction with parkin. At least 250 flies were scored for each allele tested. Alleles used were: park$^{25}$, CG2789$^{EY00814}$, CG12505$^{BG01371}$, GstE1$^{BG02858}$, Dgp-1$^{BG00396}$, Map205$^{KG05618}$, and CG16820$^{KG06079}$.

To look for genetic interactions, available mutations in genes identified by array analysis were obtained and crossed with the parkin stocks. The percentage of parkin mutants vs. controls was determined in a genetic background heterozygous or homozygous for alleles of array-identified genes. The viability of the array-gene allele as a homozygote was determined to account for any reduction in viability due to that allele alone. In the case of the genes GstE1, CG2789, CG12505, and Dgp-1, being heterozygous or homozygous for loss-of-function alleles of these genes substantially reduced the viability of parkin mutants (Table 4 and FIG. 5). This would be expected as these genes are up-regulated in parkin mutants, indicating they may play a protective role.

In the case of Map205, there was no reduction in viability in the heterozygous state, and only a slight decrease in viability when this allele was homozygous. This lack of interaction is difficult to interpret as the effect of the allele on Map205 expression is unknown. In the case of an allele of CG16820, being heterozygous for this allele seemed to offer some protection as the percentage of parkin mutants increased to 36% in this genetic background, which corresponds well to the expected Mendelian percentage of 33%. This makes sense in that transcripts of this gene are decreased in parkin mutant pupae arrays, indicating down-regulation of CG16820 may be protective to parkin mutants. However, making this allele homozygous reduced parkin mutant viability dramatically, which conflicts with this hypothesis. In all cases where reduction in viability was seen, it is likely due to an interaction between parkin and the array-identified gene as the alleles of these genes used did not have substantial effects on viability on their own. These results further support the involvement of these genes in parkin pathogenesis.

TABLE 4

Genetic interactions between parkin and array-identified genes.

| Genetic background | array gene +/− | array gene −/− | expected if no interaction |
|---|---|---|---|
| park$^{25}$ only | 25 | 25 | n/a |
| CG2789$^{EY00814}$ | 16 | 0 | 14 |
| CG12505$^{BG01371}$ | 15 | 0 | 17 |
| GstE1$^{BG02858}$ | 0 | 0 | 0 |
| Dgp-1$^{BG00396}$ | 0 | 0 | 0 |
| Map205$^{KG05618}$ | 22 | 19 | 18 |
| CG16820$^{KG06079}$ | 36 | 1 | 29 |

Shown are percentages of parkin mutants of total flies eclosing in either a heterozygous or homozygous array gene allele background. Expected numbers are calculated based on the effect on viability of making the array allele homozygous in a parkin wild-type background.

Example 6

Genetic Screen for Parkin Modifiers

To identify pathways relevant to parkin pathogenesis, a screen for genetic modifiers was initiated. As the results from testing interactions between parkin and array-identified genes were promising, the parkin partial lethality phenotype was used as a basis for this screen. This phenotype appears to be related to muscle dysfunction as the partial lethality can be rescued by ectopic expression of parkin in muscle.

The screen for modifiers was carried out by crossing a collection of P element transposon insertions into a parkin mutant background and scoring for suppression or enhancement of the partial lethality phenotype. The collection of Enhancer P (EP) transposon insertion lines makes use of a transposon that contains GAL4-responsive promoter sequences at one end which allows over-expression of the sequences the transposon has inserted adjacent to. This strategy takes advantage of the propensity of P element transposons to insert into the 5' ends of genes, often in the 5' UTR. The resulting insertions, then, can either be used to drive over-expression of the downstream genes when crossed to a GAL4-producing strain (if oriented correctly), or they can disrupt the normal function of the gene due to their insertion. When crossed to GAL4-producing strains, these EP elements can be screened to look for modification of phenotypes of interest. The mesodermal GAL4 driver 24B-GAL4, which fully rescues the partial lethality by expression of a parkin cDNA, was used to drive expression from the transposons in this screen.

The EP insertions used in this analysis are distributed among the X, 2$^{nd}$ and 3$^{rd}$ chromosomes of Drosophila. As the parkin gene resides on chromosome 3, only EP insertions on the X and 2$^{nd}$ chromosome (approximately 1,400 total) were used in the screen for modification of partial lethality, which is a parkin loss-of-function phenotype. The 1,000 EP lines which reside on chromosome 3 were analyzed in a parkin heterozygous background. Although parkin heterozygotes lack a detectable phenotype, this strategy was used to attempt to identify parkin enhancers. No modifiers were recovered from the haploinsufficiency 3$^{rd}$ chromosome screen.

To screen the insertions on the X (FIG. 6, Panel B) and 2$^{nd}$ (FIG. 6, Panel A) chromosomes, a two generation crossing scheme was used. Flies bearing the 24B-GAL4, the EP being tested, and two copies of the park$^{25}$ allele were compared to flies bearing the 24B-GAL4, the EP, and one copy of the park$^{25}$ allele to account for any effects on viability due to expression from the EP. To score modification of the partial lethality, a ratio of parkin heterozygotes to homozygotes was obtained for each EP line.

P element insertions found to increase or decrease the number of parkin homozygotes by 2 standard deviations from the expected outcome were considered modifiers. Those lines whose ratio was greater than that of the mean were considered enhancers as there were fewer parkin mutant progeny than expected, and those lines whose ratio was less than that of the mean were considered suppressors as more mutant progeny than expected were produced. To meet the two standard deviation requirement, the ratio for enhancers was more than 2.2 control:1 parkin mutant while for suppressors, the ratio was less than 1 control:2 parkin mutants. All putative modifiers recovered from screening were retested at least twice and must have met the same degree of modification to be included in the final results.

This screen led to the recovery of a total of 15 modifiers (Table 5). These modifiers make up approximately 1.1% of all the lines screened. To test whether the observed modification results from over-expression of flanking genes (gain-of-function enhancers or suppressors) or from insertional inactivation by the EP P element insertion (loss-of-function enhancers or suppressors), the effects of EP modifiers on the parkin lethality were explored in the absence of a GAL4 driver. The results of these analyses are included in Table 5.

TABLE 5

Modifier loci recovered from EP screen

| EP number | Gene | Function | Strength of modification[1] |
|---|---|---|---|
| | | Gain of function suppressors | |
| 2649 | RluA-1 | vitamin B2 biosynthesis | ***** |
| 2439 | Sano | unknown | **** |
| 2599 | EP2599 | unknown | **** |
| | | Loss of function suppressors | |
| 2210 | Tsp42Ea | unknown | **** |
| 1174 | CG14045 | PDZ, Db1, C2 domains | **** |
| | | Loss of function enhancers | |
| 828 | GstS1 | glutathione transferase, peroxidase | *********** |
| 2252 | Trx-2 | thiol-disulfide exchange/redox homeostasis | ***** |
| 670 | GstS1 | glutathione transferase, peroxidase | **** |
| | | Gain of function enhancers | |
| 2241 | Dg | muscle structure component | ******* |
| 2057 | CG13322 | unknown | ****** |
| 2594 | Dpld | transcription regulator | ****** |
| 2120 | CG14350 | unknown | ***** |
| 2188 | RpS13 | ribosomal protein S13 | ***** |

TABLE 5-continued

Modifier loci recovered from EP screen

| EP number | Gene | Function | Strength of modification[1] |
|---|---|---|---|
| 2429 | Thor | elongation factor binding, immune response | **** |
| 968 | CG8929 | unknown | **** |

[1]Each asterisk represents 0.5 standard deviations from the mean.

The identified modifiers represent genes active in a variety of functional pathways. The most striking finding from this study is that all three of the loss-of-function enhancers recovered from screening involve oxidative stress response components. One of the enhancers in this category (GstS1) had the greatest effect on parkin viability among the modifiers recovered from this screen. The identification of a second allele of GstS1 from this analysis serves as independent confirmation of its modification of parkin reduced viability.

Results from both the genetic screen for parkin modifiers and the transcriptional profile analysis of parkin mutants indicate that oxidative stress is playing a role in Parkin pathogenesis. The most striking result from the screen was the identification of all loss-of-function enhancers as having a role in the detoxification of oxidative damage in the cell, including GstS1 and thioredoxin. The Glutathione S-Transferases and Thioredoxin are part of an important biological defense system against oxidative damage, and, in the case of the screen, loss of function of these genes enhances the partial lethality phenotype as the oxidative stress defense system is impaired. In addition, a gain of function suppressor, RluA-1, was identified which has a role in vitamin B2 biosynthesis. Vitamin B2 has antioxidant activity, and a recent study has shown that vitamin B2 can have a beneficial effect to patients suffering from PD.

Several of the up-regulated genes in parkin mutants indicate that parkin mutants might be under oxidative stress. The induction of a glutathione S-transferase, a putative oxidoreductase, and cytochrome P450 all point to the mismanagement of electrons in parkin mutants and the cells' response to them. Interestingly, a two glutathione S-transferases were recently found in an allelic association study to play a role in modification of age of onset of Parkinson's disease and Alzheimer's disease, providing further evidence for the role of GSTs in PD.

Another gene identified as up-regulated in parkin mutant pupae, Dgp-1, was recently shown to be up-regulated in *Drosophila* that have been challenged with paraquat, an inducer of oxidative damage. Interestingly, this study also found up-regulation of Thor, a translational regulator, under these conditions and showed that mutants in Thor are especially sensitive to paraquat stress. Thor was identified in the genetic screen, although it was identified as a gain-of-function enhancer, which is not consistent with the paraquat data, it suggests that this protein may also be important in Parkin pathogenesis.

Example 7

Analysis of Dopaminergic Neuron Loss

In a previous study dopaminergic (DA) neuron integrity was analyzed in parkin mutants by comparing the number of tyrosine hydroxylase (TH) positive neurons in paraffin imbedded head sections from parkin mutants and control animals. No neuron loss in parkin mutants was noted, although substantial sample-to-sample variation complicated a rigorous quantitative analysis. A quantitative study of DA neuron integrity in parkin mutants was repeated using confocal microscopy of whole-mount adult brains stained with antiserum to TH. Optical sections were collected at <1 µm intervals and examined sequentially to visualize all of the DA neurons in the brain. This method allowed reproducible identification of all previously reported DA neurons in the adult *Drosophila* brain, thus providing an improved, highly sensitive approach for a quantitative analysis of DA neurons in parkin mutants.

Using this method the number of neurons in each of the DA neuron clusters was compared in parkin mutants and isogenic controls. Importantly, to control for investigator bias all experiments were carried out with the experimenter blinded to the sample genotypes throughout the analysis.

Figure 6:
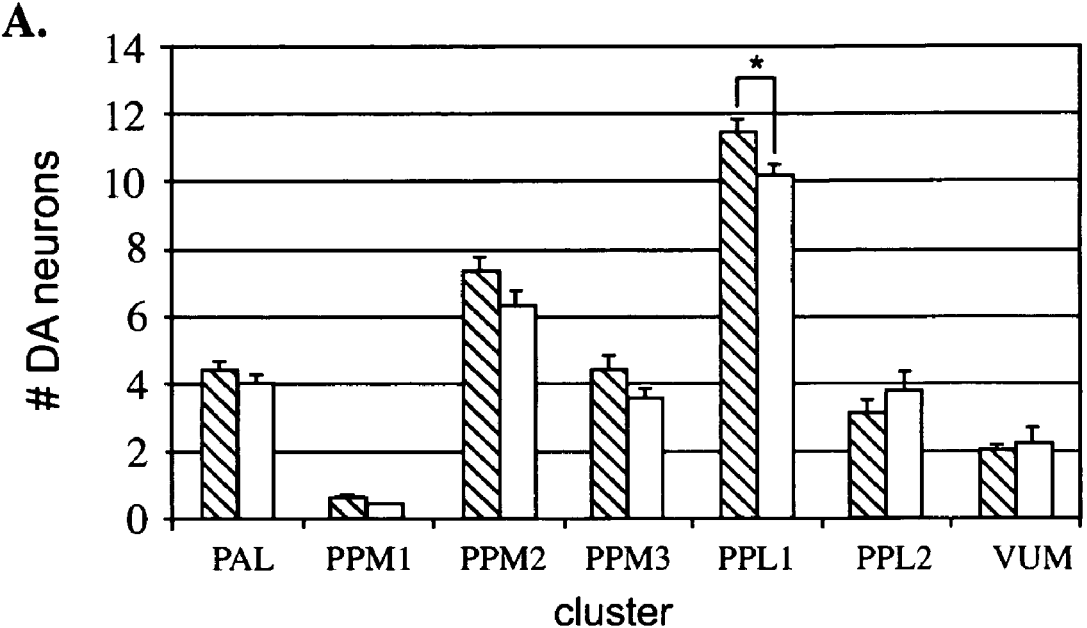
FIG. 6 shows results of dopamine neuron staining (WT and representative parkin mutant) of the clusters at 1 day (Panel A) and 20 days (Panel B).
Figure 6:
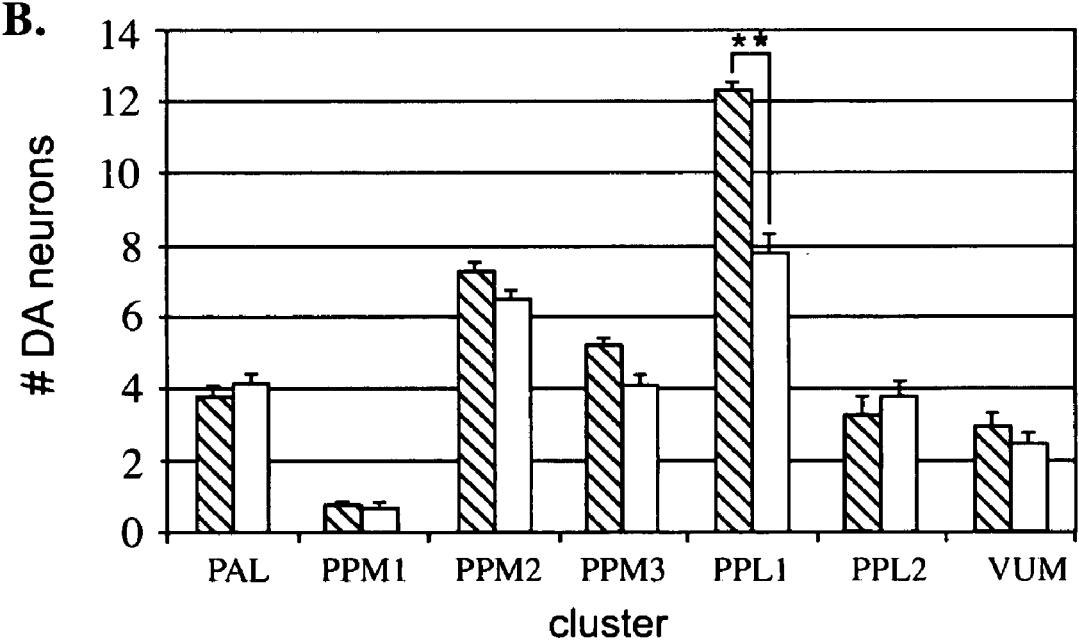

Overall neuronal integrity was well preserved in the brain of 1-day old parkin mutants, and the number of neurons in most of the DA neuron clusters was not significantly different between parkin mutants and control animals. However, significantly fewer neurons were detected in the PPL1 cluster of 1-day old parkin mutants relative to age-matched controls (FIG. 6, Panel A). Furthermore, the DA neurons of the PPL1 cluster showed an age dependent degeneration. In 20-day old parkin adults, the PPL1 neurons showed a further decrease in numbers (FIG. 6, Panel B). Again no significant difference was detected in any other cluster. In addition, no neuron loss was detected in the PPL1 cluster in parkin mutants during the late pupal stage of development. These data indicate that loss of Parkin function in *Drosophila* results in the progressive degeneration of DA neurons specifically in the PPL1 cluster.

Figure 7:
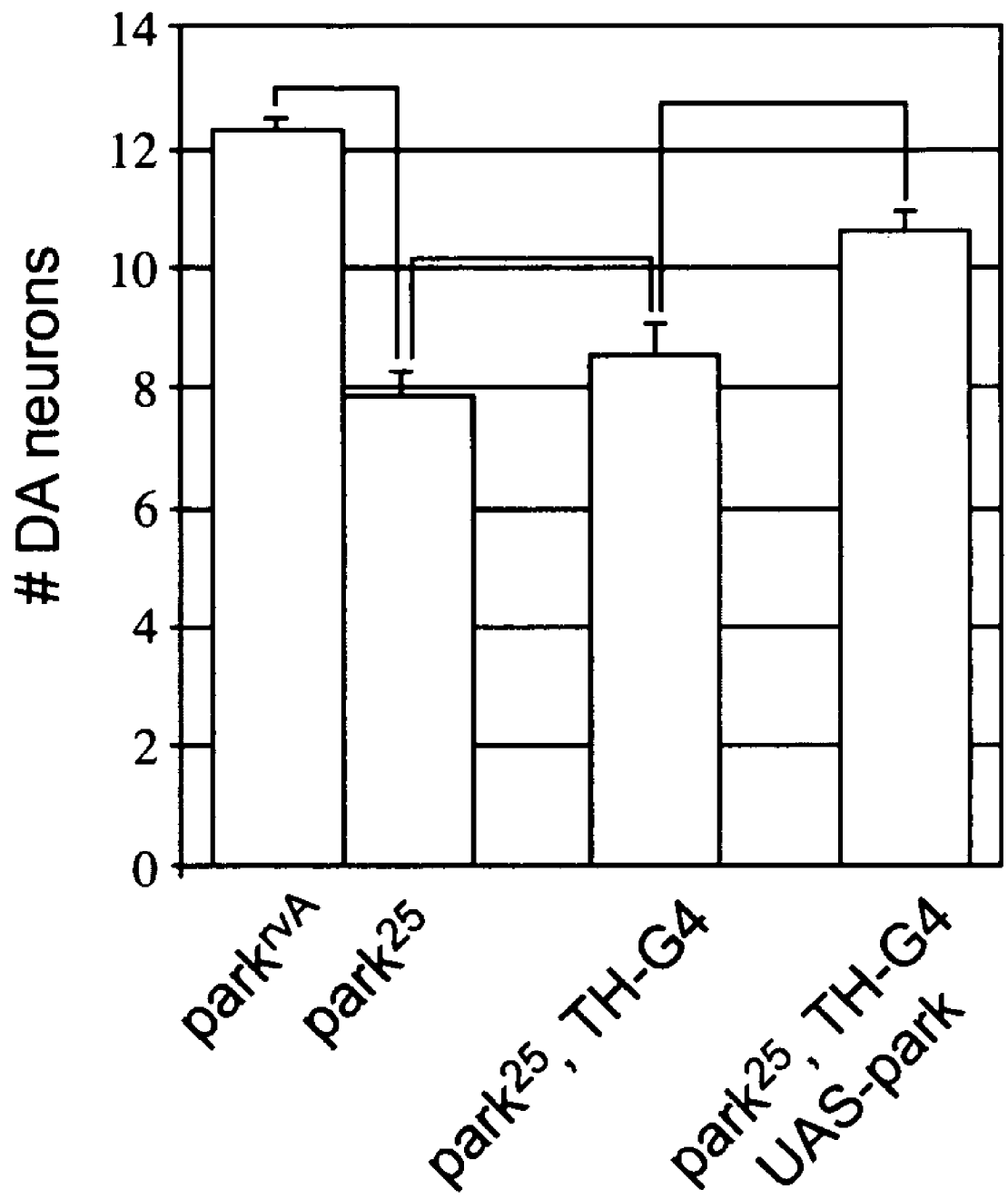
FIG. 7 shows results of PPL1 only DA neuron loss at pupal, 1 day and 20 days plus rescue with TH-GAL4.

To test whether Parkin acts in a cell autonomous fashion to prevent DA neurodegeneration, rescue of DA neuron loss was attempted by driving expression of a parkin transgene in DA neurons. The DA neuron specific TH-GAL4 was used to drive expression of a parkin transgene (UAS-park). Results of this analysis revealed that transgenic expression of Parkin in DA neurons significantly attenuated DA neuron loss in the PPL1 cluster, showing that Parkin is required in a cell-autonomous manner for DA neuron integrity (FIG. 7). Moreover, this result provides further evidence that the observed DA neuron loss in parkin mutants results specifically from loss of Parkin function.

Neurodegeneration in PD is largely restricted to a subset of DA neurons. To evaluate the specificity of neuron loss in *Drosophila* parkin mutants the integrity of other catecholaminergic neurons was also assessed. Antiserum against 5-hydroxy tyrosine was used to analyze serotonergic neurons. In contrast to results with DA neurons, no neuron loss was observed in any of the serotonergic clusters in the adult *Drosophila* brain at 20 days of age in parkin mutants. These results, in conjunction with our previous work, clearly indicate that neurodegeneration in parkin mutants is restricted to a subset of DA neurons in the central nervous system.

In an effort to identify genetic pathways that influence the *Drosophila* parkin phenotypes, an unbiased genetic screen for modifiers of a parkin partial pupal lethality was performed. A loss-of-function allele of GstS1 was the strongest enhancer recovered from this screen. To further assess the involvement of GstS1 in parkin pathology, additional GstS1 alleles on other parkin phenotypes were analyzed. All GstS1 alleles tested showed that loss of one copy of GstS1 also enhanced the climbing defect of parkin mutants. Heterozygous mutations of GstS1 alone had no effect on climbing ability.

Figure 8:
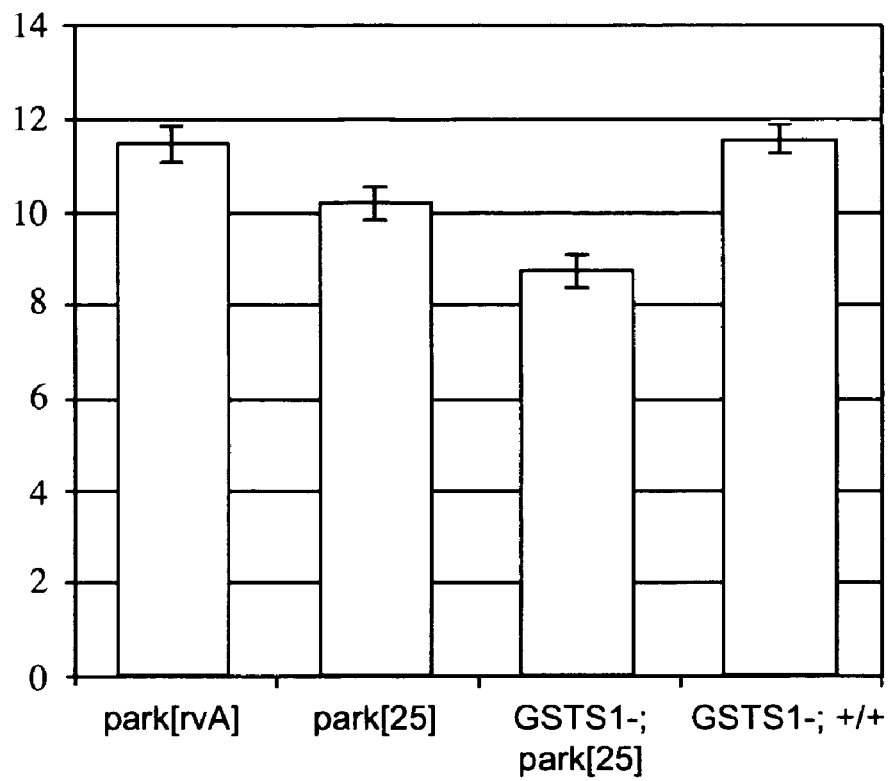
FIG. 8 shows effects of GstS1 loss-of-function (Panel A) and over-expression alleles on the parkin DA neuron loss (Panel B).
Figure 8:
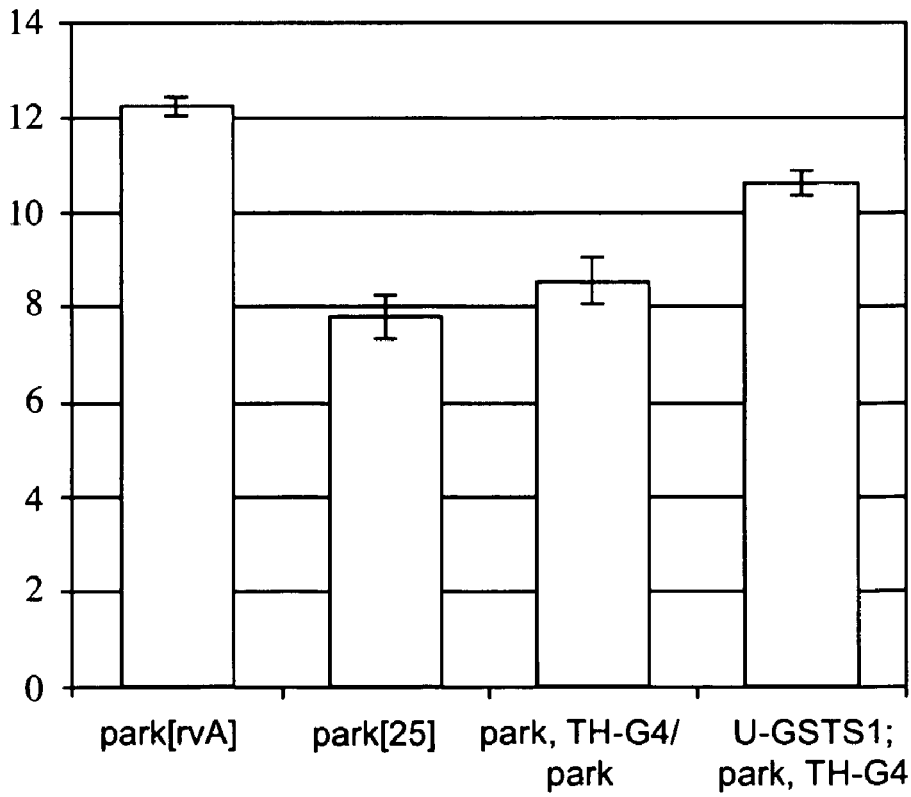

To extend these findings to the neurodegenerative phenotype, the effect of complete loss-of-function or over-expression of GstS1 on DA neurons in parkin mutants was analyzed. A null allele, $GstS1^{M26}$, in trans to deficiency Df(2R)ED1 caused an enhancement of the loss of PPL1 neurons in parkin mutants (FIG. 8, Panel A). Loss of GstS1 function alone did not affect DA neuron viability. Conversely, transgenic over-expression of GstS1 in DA neurons using TH-GAL4 was able to significantly attenuate the loss of DA neurons in 20-day parkin mutants. Moreover, the degree of rescue was comparable to that observed with transgenic parkin expression (compare with FIG. 8, Panel B). These results indicate that GstS1 is an potent factor in modulating neuron viability in a parkin mutants. Furthermore, elevated GstS1 activity is sufficient to abrogate the toxic consequence of loss of parkin function and significantly protect neuronal survival.

GstS1 is an important component in the cellular response to oxidative damage, and altered glutathione metabolism and oxidative stress are thought to be causative factors in sporadic PD. Results demonstrating GstS1 modification of the parkin loss-of-function phenotypes shows that parkin plays a protective role from the harmful effects of reactive oxygen species. To directly investigate this hypothesis, parkin mutants were tested for evidence of oxidative stress. A signature characteristic of increased oxidative stress is the production of protein carbonyls. Therefore, relative levels of protein carbonyl content were examined in parkin mutants and isogenic controls. Results of this analysis indicated that parkin mutants have significantly elevated levels of protein carbonyl content. In contrast, no significant alterations in the levels of reduced glutathione were detected in parkin mutants indicating that oxidative damage is not simply a result of decrease glutathione levels.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A *Drosophila melanogaster* model for Parkinson's disease comprising a non-functional mutant parkin gene and a non-functional mutant of at least one non-parkin gene selected from the group consisting of GstS1, GstE1, CG2789, CG12505, CG16820 and Dgp-1.

2. The model of claim 1, wherein the *Drosophila melanogaster* is homozygous for a non-functional mutant parkin gene.

3. The model of claim 1, wherein the *Drosophila melanogaster* is heterozygous for a non-functional mutant parkin gene.

4. The model of claim 1, wherein *the Drosophila melanogaster* is homozygous for a non-functional mutant of at least one non-parkin gene selected from the group consisting of GstS1, GstE1, CG2789, CG12505, CG16820 and Dgp-1.

5. The model of claim 1, wherein the *Drosophila melanogaster* is heterozygous for a non-functional mutant of at least one non-parkin gene selected from the group consisting of GstS1, GstE1, CG2789, CG12505, CG16820 and Dgp-1.

* * * * *

UNITED STATES PATENT AND TRADEMARK OFFICE
CERTIFICATE OF CORRECTION

| | |
|---|---|
| PATENT NO. | : 7,402,726 B2 |
| APPLICATION NO. | : 11/054358 |
| DATED | : July 22, 2008 |
| INVENTOR(S) | : Leo J. Pallanck |

It is certified that error appears in the above-identified patent and that said Letters Patent is hereby corrected as shown below:

In column 1, line 15, please replace "may have" with "has" so that the paragraph reads as follows:

GOVERNMENT RIGHTS

This invention was made with government support under federal grant Nos. 1RO1NS41780-01 awarded by National Institutes of Health. The United States Government has certain rights in this invention.

Signed and Sealed this

Seventeenth Day of February, 2009

JOHN DOLL
*Acting Director of the United States Patent and Trademark Office*